(12) United States Patent
Sanghera et al.

(10) Patent No.: US 7,783,340 B2
(45) Date of Patent: Aug. 24, 2010

(54) SYSTEMS AND METHODS FOR SENSING VECTOR SELECTION IN AN IMPLANTABLE MEDICAL DEVICE USING A POLYNOMIAL APPROACH

(75) Inventors: Rick Sanghera, San Clemente, CA (US); Venugopal Allavatam, Oceanside, CA (US)

(73) Assignee: Cameron Health, Inc., San Clemente, CA (US)

( * ) Notice: Subject to any disclaimer, the term of this patent is extended or adjusted under 35 U.S.C. 154(b) by 602 days.

(21) Appl. No.: 11/623,472

(22) Filed: Jan. 16, 2007

(65) Prior Publication Data

US 2008/0172100 A1    Jul. 17, 2008

(51) Int. Cl.
*A61B 5/04* (2006.01)
(52) U.S. Cl. .................. 600/509; 600/512; 600/513
(58) Field of Classification Search ............... 600/509, 600/512, 513, 515; 607/9, 14, 17, 27–28
See application file for complete search history.

(56) References Cited

U.S. PATENT DOCUMENTS

| | | | |
|---|---|---|---|
| 3,653,387 A | 4/1972 | Ceier | |
| 3,710,374 A | 1/1973 | Kelly | |
| 3,911,925 A | 10/1975 | Tillery, Jr. | |
| 4,030,509 A | 6/1977 | Heilman et al. | |
| 4,157,720 A | 6/1979 | Greatbatch | |
| 4,164,946 A | 8/1979 | Langer | |
| 4,184,493 A | 1/1980 | Langer et al. | |
| 4,191,942 A | 3/1980 | Long | |
| 4,210,149 A | 7/1980 | Heilman et al. | |
| RE30,387 E | 8/1980 | Denniston, III et al. | |
| 4,223,678 A | 9/1980 | Langer et al. | |

(Continued)

FOREIGN PATENT DOCUMENTS

DE    29801807    7/1998

(Continued)

OTHER PUBLICATIONS

Ge, Dingfei et al., "Cardiac Arrhythmia Classification Using Autoregressive Modeling," BioMedical Engineering OnLine, http://www.biomedical-engineering-online.com, Nov. 13, 2002, 12 pages.

(Continued)

*Primary Examiner*—Carl H Layno
*Assistant Examiner*—Jennifer Stewart
(74) *Attorney, Agent, or Firm*—Pramudji Law Group PLLC; Ari Pramudji; Mark Schroeder

(57) ABSTRACT

Methods and devices configured for analyzing sensing vectors in an implantable cardiac stimulus system. In an illustrative example, a first sensing vector is analyzed to determine whether it is suitable, within given threshold conditions, for use in cardiac event detection and analysis. If so, the first sensing vector may be selected for detection and analysis. Otherwise, and in other examples, one or more additional sensing vectors are analyzed. A polynomial may be used during analysis to generate a metric indicating the suitability of the sensing vector for use in cardiac event detection and analysis. Additional illustrative examples include systems and devices adapted to perform at least these methods, including implantable medical devices, and/or programmers for implantable medical devices, and/or systems having both programmers and implantable medical devices that cooperatively analyze sensing vectors.

20 Claims, 21 Drawing Sheets

U.S. PATENT DOCUMENTS

| | | |
|---|---|---|
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,550,502 A | 11/1985 | Grayzel |
| 4,567,900 A | 2/1986 | Moore |
| 4,589,420 A | 5/1986 | Adams et al. |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 4,960,126 A * | 10/1990 | Conlon et al. ............... 600/336 |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,137,025 A | 8/1992 | Turner, II |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,271,411 A | 12/1993 | Ripley et al. |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,370,667 A | 12/1994 | Alt |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,441,185 A | 8/1995 | Dragos |
| 5,447,521 A | 9/1995 | Anderson et al. |
| 5,476,503 A | 12/1995 | Yang |
| 5,501,702 A | 3/1996 | Plicchi et al. |
| 5,509,923 A | 4/1996 | Middleman et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,558,098 A | 9/1996 | Fain |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,999,853 A | 12/1999 | Stoop et al. |
| 6,014,586 A | 1/2000 | Weinberg et al. |
| 6,026,325 A | 2/2000 | Weinberg et al. |
| 6,029,086 A | 2/2000 | Kim et al. |
| 6,044,297 A | 3/2000 | Sheldon et al. |
| 6,058,328 A | 5/2000 | Levine et al. |
| 6,093,173 A | 7/2000 | Balceta et al. |
| 6,095,987 A | 8/2000 | Shmulewitz et al. |
| H001905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,185,450 B1 | 2/2001 | Seguine et al. |
| 6,266,554 B1 | 7/2001 | Hsu et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,334,071 B1 | 12/2001 | Lu |
| 6,345,198 B1 | 2/2002 | Mouchawar et al. |
| 6,411,844 B1 | 6/2002 | Kroll et al. |
| 6,493,579 B1 | 12/2002 | Gilkerson et al. |
| 6,493,584 B1 | 12/2002 | Lu |
| 6,496,715 B1 | 12/2002 | Lee et al. |
| 6,516,225 B1 | 2/2003 | Florio |
| 6,567,691 B1 | 5/2003 | Stadler |
| 6,574,505 B1 | 6/2003 | Warren |
| 6,625,490 B1 | 9/2003 | McClure et al. |
| 6,647,292 B1 | 11/2003 | Bardy et al. |
| 6,684,100 B1 | 1/2004 | Sweeney et al. |
| 6,687,540 B2 | 2/2004 | Marcovecchio |
| 6,699,200 B2 | 3/2004 | Cao et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,810,284 B1 | 10/2004 | Bradley |
| 6,834,204 B2 | 12/2004 | Ostroff et al. |
| 6,856,835 B2 | 2/2005 | Bardy et al. |
| 6,865,417 B2 | 3/2005 | Rissmann et al. |

| Patent No. | Date | Inventor |
|---|---|---|
| 6,866,044 B2 | 3/2005 | Bardy et al. |
| 6,892,092 B2 | 5/2005 | Palreddy et al. |
| 6,909,916 B2 | 6/2005 | Spinelli et al. |
| 6,927,721 B2 | 8/2005 | Ostroff et al. |
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,959,212 B2 | 10/2005 | Hsu et al. |
| 6,975,904 B1 | 12/2005 | Sloman |
| 6,980,856 B2 | 12/2005 | Sullivan et al. |
| 6,988,003 B2 | 1/2006 | Bardy et al. |
| 6,996,434 B2 | 2/2006 | Marcovecchio et al. |
| 7,016,730 B2 | 3/2006 | Ternes |
| 7,020,523 B1 | 3/2006 | Lu et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,039,459 B2 | 5/2006 | Bardy et al. |
| 7,039,463 B2 | 5/2006 | Marcovecchio |
| 7,039,465 B2 | 5/2006 | Bardy et al. |
| 7,043,299 B2 | 5/2006 | Erlinger et al. |
| 7,062,329 B2 | 6/2006 | Ostroff |
| 7,065,407 B2 | 6/2006 | Bardy et al. |
| 7,065,410 B2 | 6/2006 | Bardy et al. |
| 7,069,080 B2 | 6/2006 | Bardy et al. |
| 7,076,294 B2 | 7/2006 | Bardy et al. |
| 7,076,296 B2 | 7/2006 | Rissmann et al. |
| 7,090,682 B2 | 8/2006 | Sanders et al. |
| 7,092,754 B2 | 8/2006 | Bardy et al. |
| 7,120,495 B2 | 10/2006 | Bardy et al. |
| 7,120,496 B2 | 10/2006 | Bardy et al. |
| 7,130,689 B1 | 10/2006 | Turcott |
| 7,146,212 B2 | 12/2006 | Bardy et al. |
| 7,149,575 B2 | 12/2006 | Ostroff et al. |
| 7,167,747 B2 | 1/2007 | Gunderson et al. |
| 7,181,274 B2 | 2/2007 | Rissmann et al. |
| 7,181,281 B1 | 2/2007 | Kroll |
| 7,266,409 B2 | 9/2007 | Gunderson |
| 7,412,287 B2 | 8/2008 | Yonce et al. |
| 2001/0034487 A1 | 10/2001 | Cao et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2002/0165587 A1* | 11/2002 | Zhang et al. ............... 607/28 |
| 2002/0169484 A1 | 11/2002 | Mathis et al. |
| 2003/0088277 A1 | 5/2003 | Rissmann et al. |
| 2003/0204215 A1* | 10/2003 | Gunderson et al. ........... 607/27 |
| 2004/0230243 A1 | 11/2004 | Haefner et al. |
| 2004/0254611 A1 | 12/2004 | Palreddy et al. |
| 2004/0254613 A1 | 12/2004 | Ostroff et al. |
| 2005/0049644 A1 | 3/2005 | Warren et al. |
| 2005/0192507 A1 | 9/2005 | Warren et al. |
| 2006/0085038 A1 | 4/2006 | Linder et al. |
| 2006/0167502 A1 | 7/2006 | Haefner |
| 2007/0123947 A1 | 5/2007 | Wenger et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239044 A1 | 10/2007 | Ghanem et al. |
| 2007/0239045 A1 | 10/2007 | Ghanem et al. |
| 2007/0239046 A1 | 10/2007 | Ghanem et al. |
| 2007/0239047 A1 | 10/2007 | Ghanem et al. |
| 2007/0239048 A1 | 10/2007 | Ghanem et al. |
| 2007/0239049 A1 | 10/2007 | Ghanem et al. |
| 2007/0239050 A1 | 10/2007 | Ghanem et al. |
| 2007/0239051 A1 | 10/2007 | Ghanem et al. |
| 2007/0239220 A1 | 10/2007 | Greenhut et al. |
| 2007/0270704 A1 | 11/2007 | Ghanem et al. |
| 2008/0188901 A1 | 8/2008 | Sanghera et al. |
| 2008/0269813 A1 | 10/2008 | Greenhut et al. |
| 2008/0275521 A1 | 11/2008 | Warren et al. |
| 2009/0093731 A1 | 4/2009 | Palreddy et al. |

FOREIGN PATENT DOCUMENTS

| | | |
|---|---|---|
| EP | 0095727 | 12/1983 |
| EP | 0316616 | 5/1989 |
| EP | 0347353 | 12/1989 |
| EP | 0517494 | 12/1992 |
| EP | 0518599 | 12/1992 |
| EP | 0536873 | 4/1993 |
| EP | 0586858 | 3/1994 |
| EP | 0627237 | 12/1994 |
| EP | 0641573 | 3/1995 |
| EP | 0677301 | 10/1995 |
| EP | 0813889 A2 | 12/1997 |
| EP | 0917887 | 5/1999 |
| EP | 0923130 | 6/1999 |
| EP | 1000634 | 5/2000 |
| EP | 1 745 741 A1 | 1/2007 |
| WO | 9319809 | 10/1993 |
| WO | 9729802 | 8/1997 |
| WO | 9825349 | 6/1998 |
| WO | 9903534 | 1/1999 |
| WO | 9937362 | 7/1999 |
| WO | WO/99/48554 A1 | 9/1999 |
| WO | 9953991 | 10/1999 |
| WO | 0041766 | 7/2000 |
| WO | 0050120 | 8/2000 |
| WO | 0143649 | 6/2001 |
| WO | 0156166 | 8/2001 |
| WO | 0222208 | 3/2002 |
| WO | 0224275 | 3/2002 |
| WO | 02068046 | 9/2002 |
| WO | 03/020367 A1 | 3/2003 |
| WO | 03018121 | 3/2003 |
| WO | 2004/091720 A2 | 10/2004 |
| WO | 2004 105871 A1 | 12/2004 |
| WO | 2007 089959 A1 | 8/2007 |
| WO | WO/03/065613 A1 | 8/2007 |
| WO | WO/2007/140207 A1 | 12/2007 |
| WO | WO/2007/140209 A2 | 12/2007 |
| WO | WO/2007/140214 A1 | 12/2007 |
| WO | WO/2007/140209 A3 | 4/2008 |

OTHER PUBLICATIONS

U.S. Appl. No. 11/441,522 to Sanghera et al., filed May 26, 2006.
U.S. Appl. No. 11/442,228 to Sanghera et al., filed May 26, 2006.
U.S. Appl. No. 11/441,516 to Sanghera et al., filed May 26, 2006.
Burii et al.; "Utility of the Surface ECG Before VDD Pacemaker Implantation"; International Journal of Cardiology; vol. 117, No. 2, pp. 211-213; 2007.
Response to Office Action (Mar. 23, 2009) and Office Action (Dec. 23, 2008); U.S. Appl. No. 11/441,522 (US 2007-0276445 A1 - Sanghera, et al).
Final Office Action (Apr. 8, 2009), Response to Office Action (Feb. 25, 2009), and Office Action (Nov. 25, 2008); U.S. Appl. No. 11/441,516 (US 2007-0276447 A1—Sanghera, et al).
Response to Office Action (Apr. 23, 2009) and Office Action (Dec. 23, 2008); U.S. Appl. No. 11/442,228 (US 2007-0276452 A1—Sanghera et al).
Office Action (Feb. 24, 2009); U.S. Appl. No. 11/672,353 (US 2008-0188901 A1—Sanghera et al).
Response to Office Action (Apr. 9, 2009) and Office Action (Jan. 12, 2009); U.S. Appl. No. 11/120,284 (US 2005-019507 A1—Warren, et al).

Bardy, Gust H. et al., "Multicenter Experience with a Pectoral Unipolar Implantable Cardioverter-Defibrillator," JACC, Aug. 1996, vol. 28, No. 2, pp. 400-410.

Friedman, Richard A. et al., "Implantable Defibrillators In Children: From Whence to Shock," Journal of Cardiovascular Electrophysiology, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, pp. 356-360.

Higgins, Steven L. et al., "The First Year Experience with the Dual Chamber ICD," PACE, Jan. 2000, vol. 23, pp. 18-25.

Mirowski, M. et al., "Automatic Detection and Defibrillation of Lethal Arrhythmias-A New Concept," JAMA, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," IEEE, (1987) pp. 167-170.

Schuder, John C., "Completely Implanted Defibrillator," JAMA, vol. 214, No. 6, Nov. 9, 1970. p. 1123 (single sheet).

Schuder, John C. et al., "Experimental Ventricular Defibrillation with an Automatic and Completely Implanted System, "Trans. Amer. Soc. Artif. Int. Organs, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schuder, John C. et al., "Standby Implanted Defibrillators," Arch Intern. Med, vol. 127, Feb. 1971, p. 317 (single sheet).

Schuder, John C. et al., "Transthoracic Ventricular Defibrillation in the Dog with Truncated and Untruncated Exponential Stimuli," IEEE Transactions on Bio-Medical Engineering, vol. BME-18, No. 6, Nov. 1971, pp. 410-415.

Schwacke, H. et al., "Komplikationen nit Sonden bei 340 Patienten mit einem Implantierbaren Kardioverter/Defibrillator," Z Kardiol (1999)vol. 88, No. 8 pp. 559-565.

Throne, Robert D., "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

Tietze U. et al., "Halbleiter-Schaltungstechnik," © Springer-Verlag (Berlin, Germany), (1991) pp. 784-786.

Valenzuela, Terrence D. et al., "Outcomes of Rapid Defibrillation by Security Officers After Cardiac Arrest in Casinos," The New England Journal of Medicine, Oct. 26, 2000, vol. 343, No. 17, pp. 1206-1209.

Walters, R.A. et al., "Analog to Digital Conversion Techniques in Implantable Devices," Annual International Conference of the IEEE Engineering in Medicine and Biology Society, vol. 13 No. 4 (1991) p. 1674-1676.

U.S. Appl. No. 60/786,981; filed Mar. 29, 2006; Stadler, et al.

U.S. Appl. No. 60/632,000; filed Dec. 1, 2004; Gunderson.

U.S. Appl. No. 60/186,235; filed Mar. 1, 2000; Cao, et al.

* cited by examiner

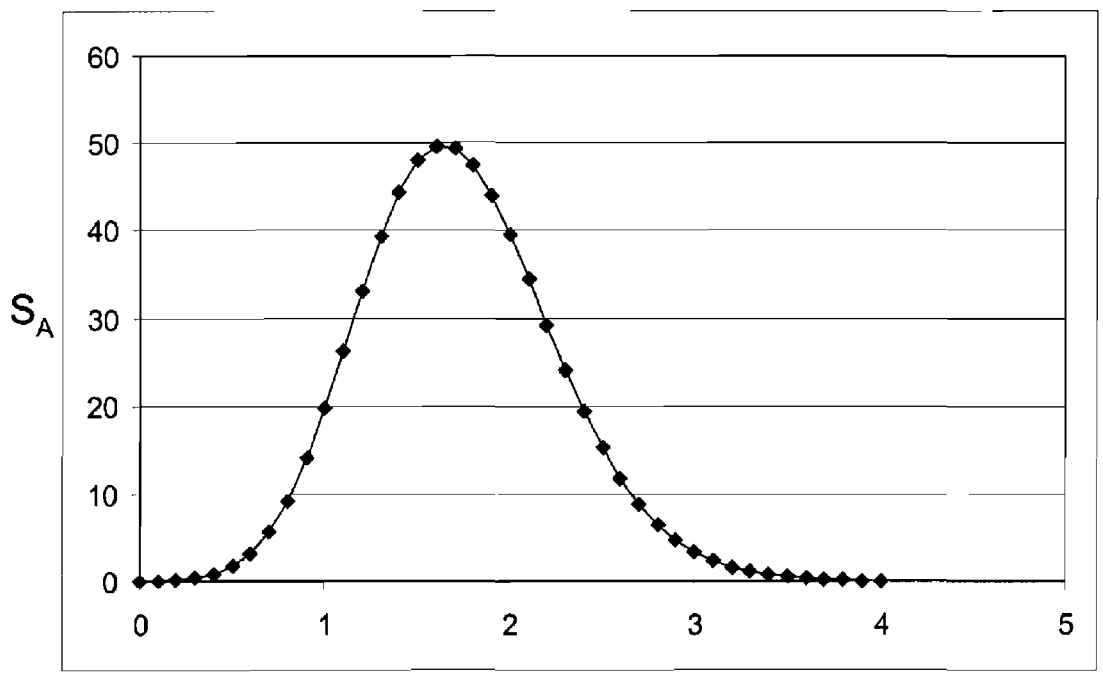
FIG. 10A QRS$_{Avg}$
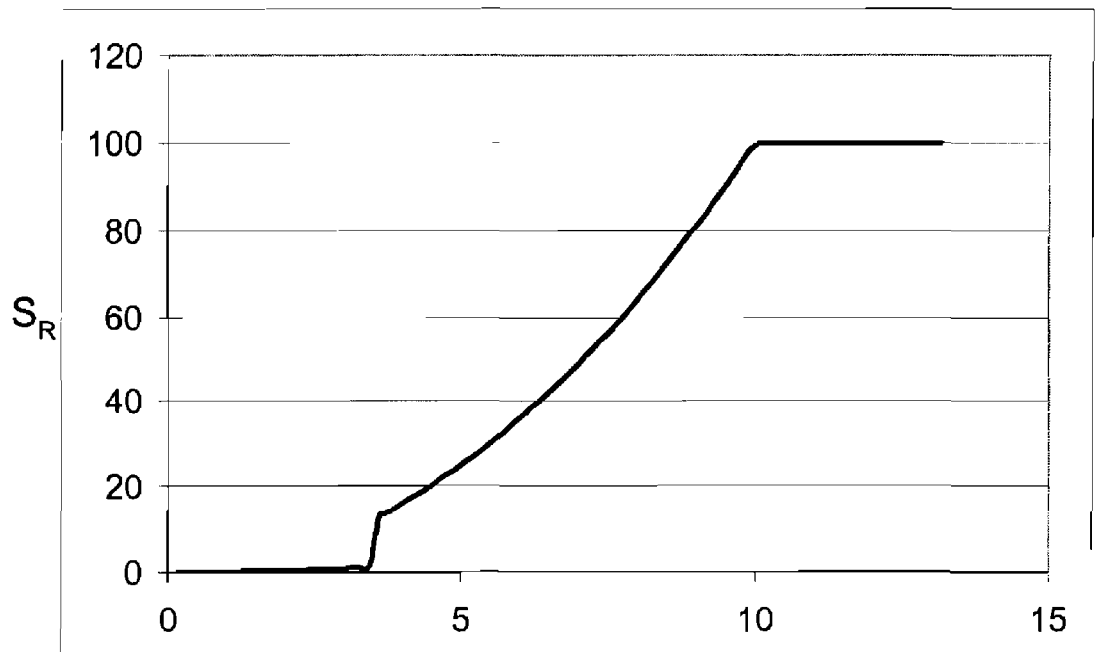
FIG. 10B SNR

US 7,783,340 B2

SYSTEMS AND METHODS FOR SENSING VECTOR SELECTION IN AN IMPLANTABLE MEDICAL DEVICE USING A POLYNOMIAL APPROACH

RELATED APPLICATIONS

This application is related to U.S. application Ser. No. 11/441,522, entitled SYSTEMS AND METHODS FOR SENSING VECTOR SELECTION IN AN IMPLANTABLE MEDICAL DEVICE; U.S. application Ser. No. 11/441,516, entitled IMPLANTABLE MEDICAL DEVICES AND PROGRAMMERS ADAPTED FOR SENSING VECTOR SELECTION; and U.S. application Ser. No. 11/442,228, entitled IMPLANTABLE MEDICAL DEVICE SYSTEMS HAVING INITIALIZATION FUNCTIONS AND METHODS OF OPERATION, each of which was filed on May 26, 2006; the disclosures of each of these Applications are incorporated herein by reference.

FIELD

The present invention relates to the field of implantable medical devices. More specifically, the present invention relates to implantable medical devices that detect cardiac activity.

BACKGROUND

Implantable cardiac stimulus devices often include circuitry for detection of electrical cardiac activity to observe a patient's cardiac function. Methods and devices adapted for identifying and/or selecting favorable sensing vectors are desired.

SUMMARY

The present invention, in illustrative examples, includes methods and devices configured for analyzing sensing vectors in an implantable cardiac stimulus system. In an illustrative example, a first sensing vector is analyzed to determine whether it is suitable, within given threshold conditions, for use in cardiac event detection and analysis. If so, the first sensing vector may be selected for detection and analysis. Otherwise, one or more additional sensing vectors are analyzed. In another illustrative embodiment, a set of sensing vectors are analyzed rather than possibly identifying a suitable vector without analyzing additional vectors. A polynomial or other mathematical formula may be used during analysis to generate a metric indicating the suitability of the sensing vector for use in cardiac event detection and analysis. A detailed illustrative example includes methods for analyzing sensing vectors by the use of a scoring system. Additional illustrative examples include systems and devices adapted to perform at least these methods. One such illustrative example includes an implantable medical device, which may be an implantable cardioverter/defibrillator, adapted to perform these methods. Another example includes a programmer configured to perform these methods including certain steps of directing operation of an associated implanted or implantable medical device. Yet another illustrative example includes a system having both an implantable device and a programmer, where steps of performing sensing vector analysis are cooperatively performed by each of the devices.

BRIEF DESCRIPTION OF THE DRAWINGS

FIGS. 10A-10C are graphs illustrating mathematical relationships used in illustrative embodiments;

DETAILED DESCRIPTION

The following detailed description should be read with reference to the drawings. The drawings, which are not necessarily to scale, depict illustrative embodiments and are not intended to limit the scope of the invention.

Figure 1A:
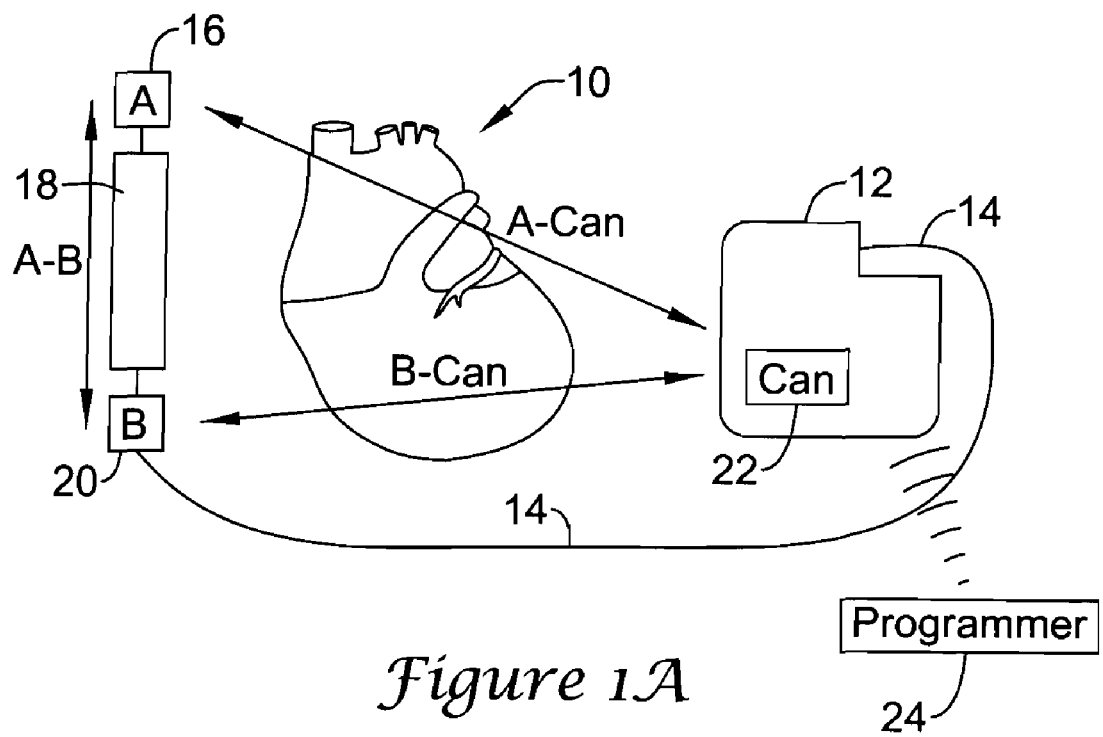
FIGS. 1A-1B, respectively, show subcutaneous and transvenous implanted cardiac stimulus systems relative to the heart.
Figure 1B:
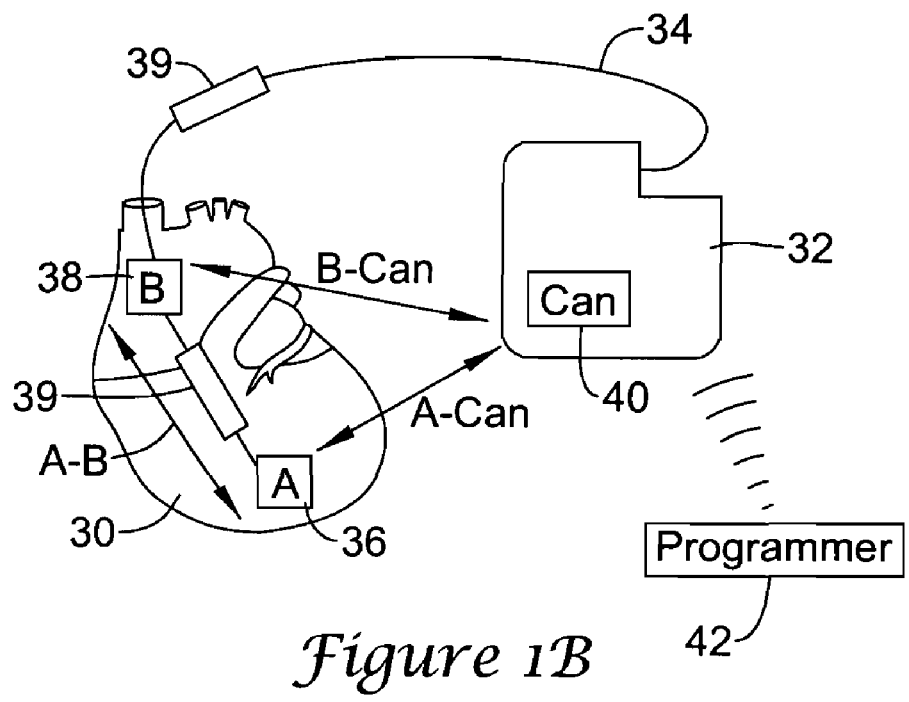

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12. Several vectors for sensing are therefore available including A-can, B-can, and A-B. It should be understood that each pair of electrodes actually makes up a first vector of a first polarity and a second vector of a second, opposite polarity; for convenience, reference is made simply to the combination of electrodes. It should be noted that the use of the coil electrode 18 as a sensing electrode is also possible. In addition to sensing cardiac activity through cardiac electrical signals, any or all of the electrodes may be used to detect respiration or other physiological activity or status. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown in FIG. 1A. A unitary system including an additional lead may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included, and also may be used for sensing in some embodiments of the present invention. In the illustrative example, electrode A 36 is located generally in the patient's ventricle, and electrode B 38 is located generally in the patient's atrium. The lead 34 may be anchored into the patient's myocardium. The lead 34 may also include one or more coil electrodes, either interior to or exterior to the heart, as shown at 39, which may be used to deliver stimulus and/or to sense cardiac or other activity, such as respiration. A can electrode 40 is shown on the canister 32. With this system, plural sensing vectors may be defined as well, in first and second polarities. In both FIGS. 1A and 1B, one or more sensing electrodes may also be used for stimulus delivery. Some embodiments of the present invention may be used in combination systems that may include sensing vectors defined between two subcutaneous electrodes, a subcutaneous electrode and a transvenous electrode, or two transvenous electrodes.

In the configurations of FIGS. 1A and 1B, there are multiple sensing vectors available. Detection of cardiac function along at least one of these sensing vectors allows the implanted cardiac stimulus system to determine whether treatment is indicated due to the detection and identification of a malignant condition such as, for example, a ventricular tachycardia. An implanting physician may perform vector selection by directly diagnosing which of the captured vectors is best. However, this requires an assessment of cardiac function along several vectors and may increase the time needed to perform implantation, and also increases the risk of human error. Further, if the physician is needed to perform vector selection, as patient physiology changes (which may happen as scarring develops around an implanted sensing electrode), the system is at risk of using a sub-optimal sensing vector until the patient re-visits the physician. Finally, the selection of a vector has often been a task requiring specialized training, as selection of a suitable vector among those available is not necessarily intuitive.

A robust sensing vector selection method is desirable, as well as devices adapted to perform such methods. The present invention, in illustrative embodiments, provides such methods and uses various criteria for doing so. Some embodiments include implantable devices and programmers for implantable devices that are adapted to perform such methods.

The systems shown in FIGS. 1A-1B may include operational circuitry and a power source housed within the respective canisters. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a bank of capacitors) for building up a stored voltage for cardiac stimulus taking the form of cardioversion and/or defibrillation. The operational circuitry may also be adapted to provide a pacing output. Both cardioversion/defibrillation and pacing sub-circuitry and capacities may be incorporated into a single device. The methods discussed below may be embodied in hardware within the operational circuitry and/or as instruction sets for operating the operational circuitry and/or in the form of machine-readable media (optical, electrical, magnetic, etc.) embodying such instructions and instruction sets.

Each of the devices 12, 32 may further include such components as would be appropriate for communication (such as RF communication or inductive telemetry) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate and/or direct and/or observe diagnostic or operational tests. After implantation, the programmer 24, 42 may be used to non-invasively determine the status and history of the implanted device. The programmer 24, 42 and the implanted device 12, 32 are adapted for wireless communication allowing interrogation of the implanted device. The programmers 24, 42 in combination with the implanted devices 12, 32 may also allow annunciation of statistics, errors, history and potential problem(s) to the user/physician.

In some embodiments, the following illustrative methods are performed directly by the implanted devices 12, 32 either independently (periodically or occasionally) or at the direction of a programmer 24, 42. In other embodiments, the following methods are performed by using the implanted devices 12, 32 to perform data capture, with the programmer 24, 42 performing other analytical steps by downloading captured data (for example, in real time, or in blocks of predetermined size). The programmer 24, 42 may prompt data capture suitable for the illustrative methods below, and the programmer 24, 42 may then direct the implanted device 12, 32 to utilize a selected vector. Some methods may be performed by distributing appropriate tasks between the implanted device 12, 32 and the programmer 24, 42.

Figure 2:
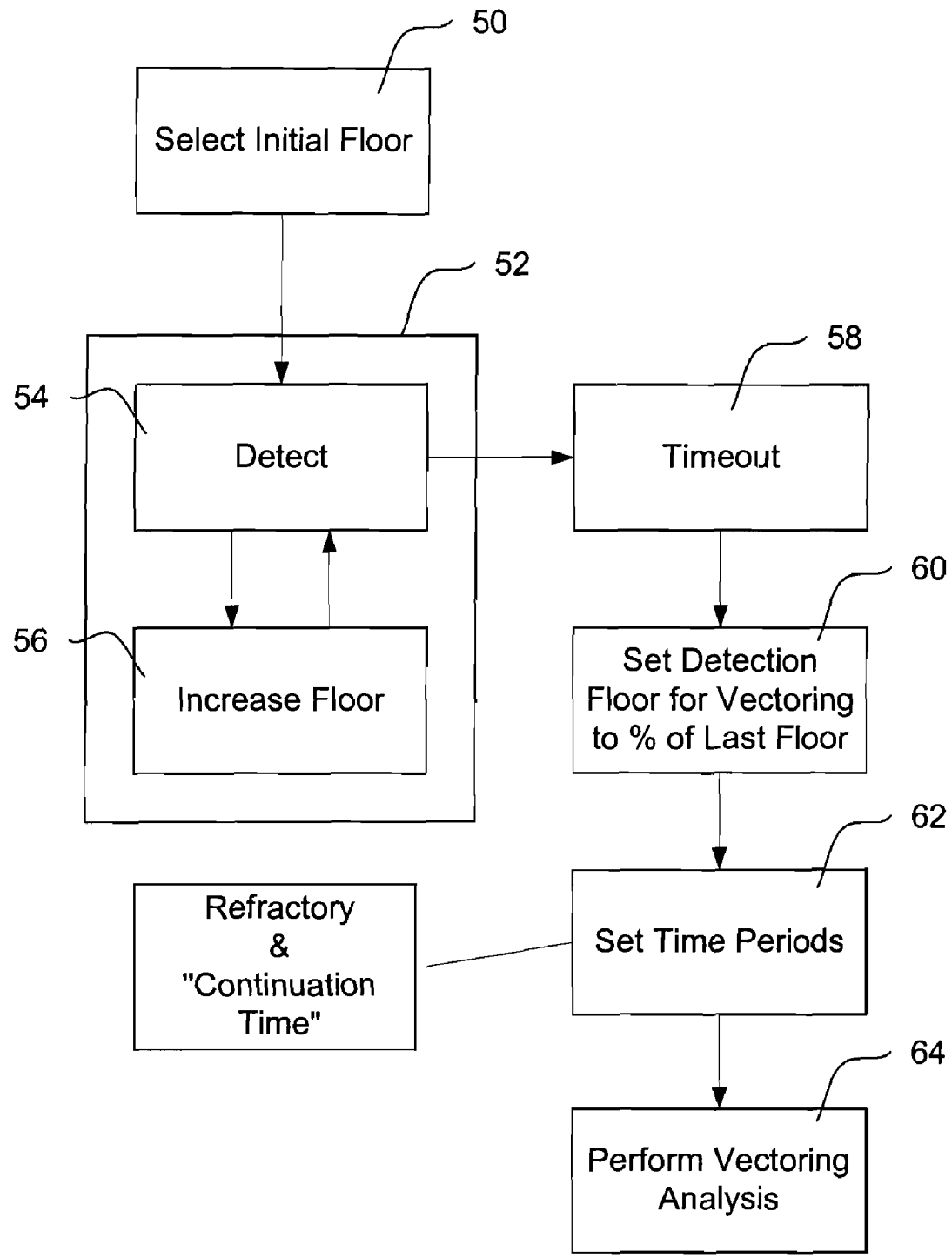
FIG. 2 is a block diagram illustrating a method of initialization for an implantable cardiac stimulus system.

FIG. 2 is a block diagram illustrating a method of detection initialization for an implantable cardiac stimulus system. For the vectoring method, a detection threshold for the implantable cardiac stimulus system is initialized by performing a process of detection with one or more available sensing vectors. For example, the method steps shown in FIG. 2 may be performed for sensing vectors A-Can, B-Can, and A-B, shown in FIGS. 1A-1B. The steps may also be performed using vectors including the shocking/coil electrode 18 shown in FIG. 1A as well as any stimulus electrodes in FIG. 1B, although the set under consideration is reduced for illustrative purposes in the following examples to A-Can, B-Can, and A-B.

A vectoring method is a method of analyzing one or more available sensing vectors to select a sensing vector for use in detection. The method in FIG. 2 is used to set the sensing parameters for a vectoring method. FIG. 2 includes first setting an initial sensing floor, as shown at 50, preferably in a relatively low range (high sensitivity) so that the device will detect cardiac events that exceed the detection floor. For example, this initial sensing floor may be set to a percentage of a historical value measured over a number of previously detected cardiac events, specific to the patient, a patient population, a particular implantation configuration, or other suitable variables.

As shown at block 52, several iterations of a sub-method are performed. In block 52, an event is detected, as shown at 54, and the detection floor is then raised, as shown at 56. The event detection 54 may occur when the detection floor is crossed by the sensed signal, and may include a refractory period during which detection is disabled. Iterations in block 52 may continue until a timeout occurs, as shown at 58. The timeout 58 may occur, for example, when a 2-second period of time expires without a detection occurring. The timeout may indicate the detection floor has been raised above the received signal strength for cardiac events.

After the timeout at 58, the vectoring detection floor is set to a percentage of the detection floor that led to the timeout 58, as shown at 60. For example, the vectoring detection floor may be set to about 40% of the level that led to the timeout. Next, time periods are set, as shown at 62, and vectoring analysis is performed as shown at 64. The time periods are explained by reference to FIGS. 3A-3B. The vectoring detection floor may be set differently for each of the sensing vectors being analyzed, since each vector may produce a different signal strength than the other vectors. For example, the method shown in FIG. 2 may be repeated for each of several vectors prior to performing any vectoring analysis 64, or the method of FIG. 2 may be performed as a part of vectoring analysis for each individual vector.

Figure 3A:
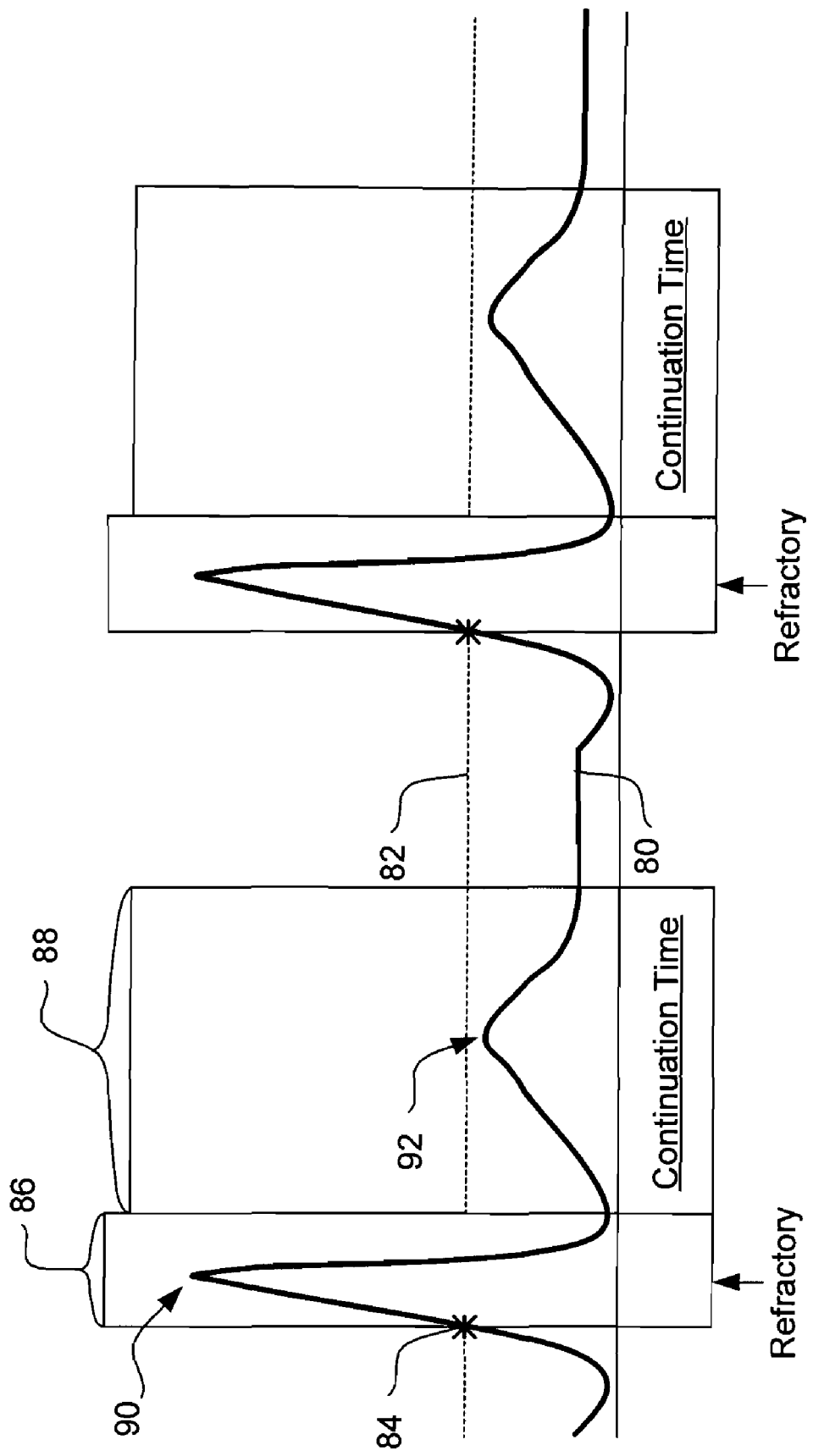
FIGS. 3A-3B are graphical representations of cardiac signals illustrating an analytical form for identifying QRS and T-Waves.

FIG. 3A is a graphical representation of a cardiac signal illustrating an analytical form for identifying QRS and T-Waves. A cardiac signal is shown at 80. A vectoring detection threshold is shown at 82. An event is detected at 84, when the cardiac signal 80 crosses the vectoring detection threshold 82. A refractory period 86 occurs following the detection 84. After the refractory period 86, a one or more continuation time (CT) period(s) occur, as shown at 88. The peak occurring during the refractory period 86 is at least initially assumed to be the R-wave, as shown at 90. A peak signal value is identified during the CT period, as shown at 92, and is assumed to be noise. This peak 92 may be the T-wave, but is not necessarily so. In an illustrative example, the refractory period 86 lasts 160 milliseconds, and the CT period(s) 88 last 220 milliseconds, although these values may vary in other embodiments.

In the illustrative example, it is assumed (for vectoring purposes) that the longest QT interval will be about 400 milliseconds, and so the peak value detected during the CT period 88 is assumed to be the T-wave. The illustrative method, with the parameters given above, is adapted for use with a patient having a heart rate of 30-150 beats-per-minute (bpm). The detection threshold 82 is effective during the CT period 88, such that, if the sensed signal crosses the detection threshold 82 during the CT period 88, this will be treated as another detection.

Figure 3B:
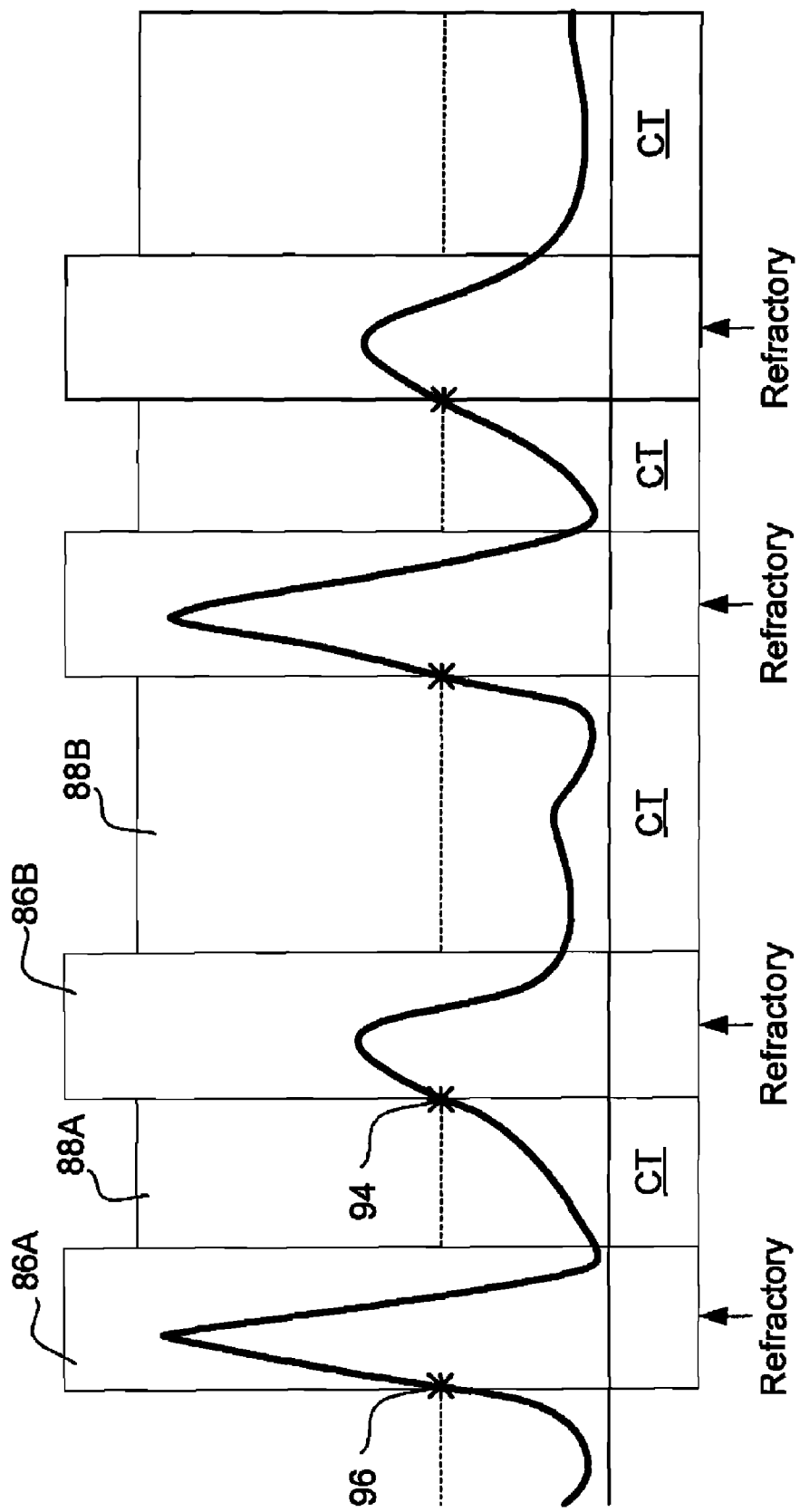

FIG. 3B illustrates that a new detection 94 will be defined for a threshold crossing during the CT period 88A that follows a first refractory period 86A associated with a first detection 96. The new detection 94 has its own refractory period 86B and CT period 88B. Given a rate of 150 bpm or less, the detections shown in FIG. 3B indicate a double detection, as the detections are too close together. It can be seen that, when double detection occurs, sensing outside of the CT periods 88A, 88B may not happen, although this is not always the case. As explained further below, the present methods are adapted to select at most one of the detections 94, 96 as representative of a heart beat, while determining that the other detection 94, 96 is noise.

Because the different sensing vectors may detect events in different forms, and because the targeted population for such devices often has abnormal cardiac function, a prototypical PQRST form, as shown in FIG. 3A, may not always occur. For example, the T-wave may be relatively larger than the R-wave. Some of the present methods also include an ability to set a flag that calls for an attending physician (the "operator") to observe the cardiac signal and determine whether the R-wave or T-wave has a greater amplitude. When certain conditions are met, the flag is set and the operator may be asked for input.

Figure 4:
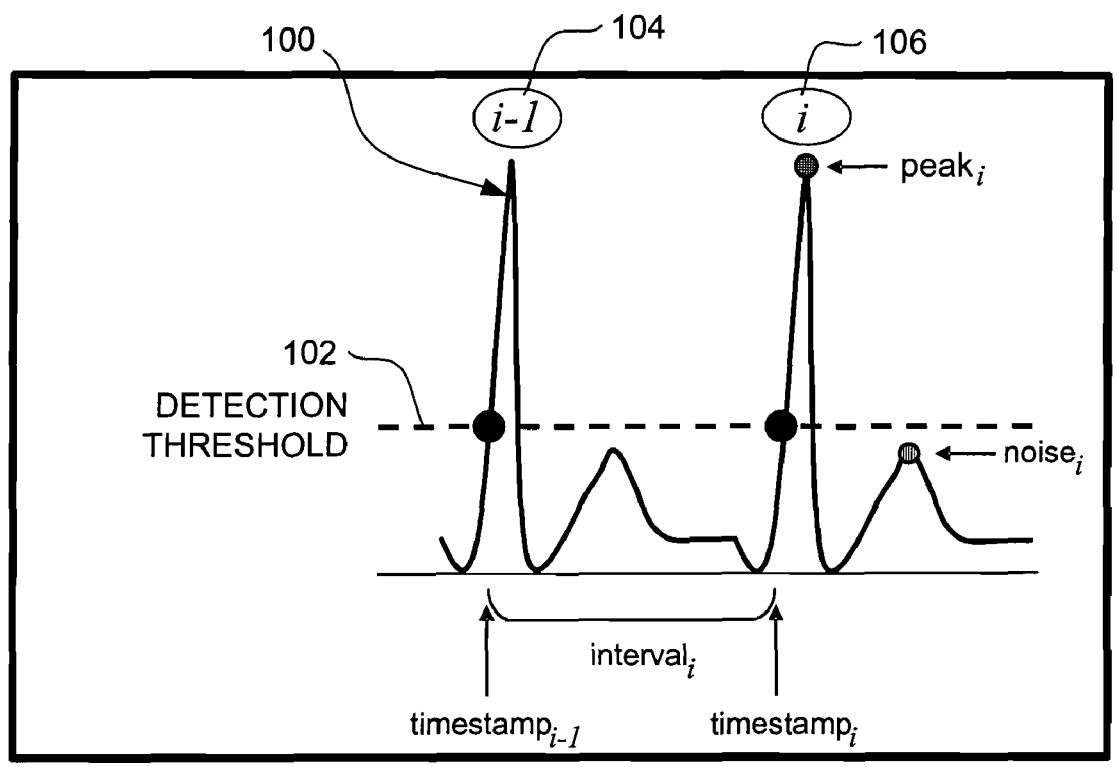
FIG. 4 is a graph showing treatment of a cardiac signal for explanatory purposes.

FIG. 4 is a graph showing treatment of a cardiac signal for explanatory purposes. During the vectoring example that follows, the captured cardiac signal is marked to identify events. The signal, shown at 100, is detected relative to a detection threshold 102. When the signal exceeds the detection threshold, this is marked as an event. The chronologically most recent event is marked event i, as shown at 106, while a contiguously prior event is marked i−1, as shown at 104. The duration of time between detections 104 and 106 is defined as interval$_i$, while the amplitude of peak 106 is peak$_i$, and the height of the noise peak following peak 106 is noise$_i$. One goal is to define the detected events and portions of the cardiac signal in a manner as shown in FIG. 4; the methods of FIGS. 5A-5B, as well as other methods shown below, are adapted to achieve this goal, when possible.

Figure 5A:
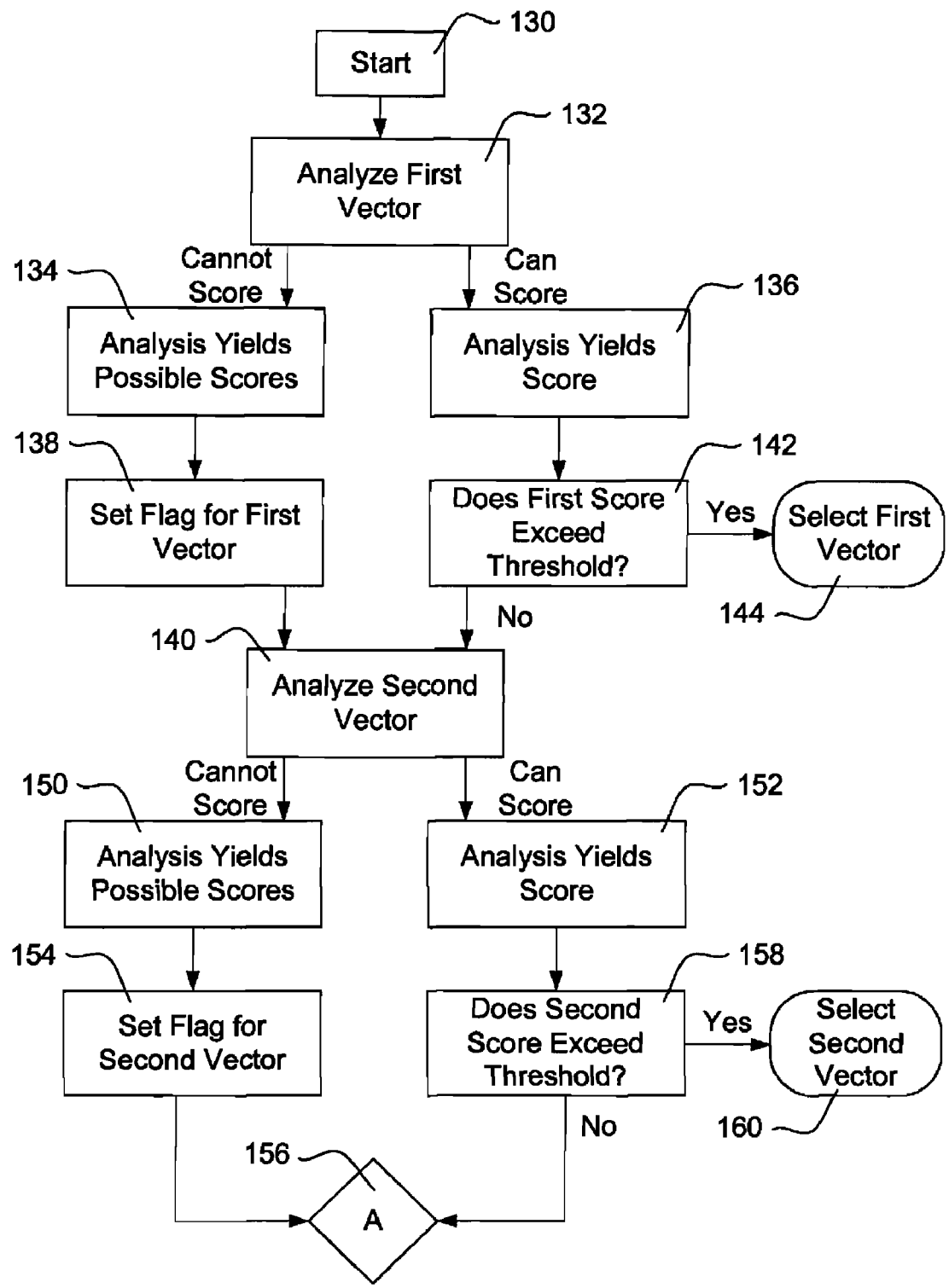
FIGS. 5A-5B illustrate a block diagram for a method of signal vector analysis.
Figure 5B:
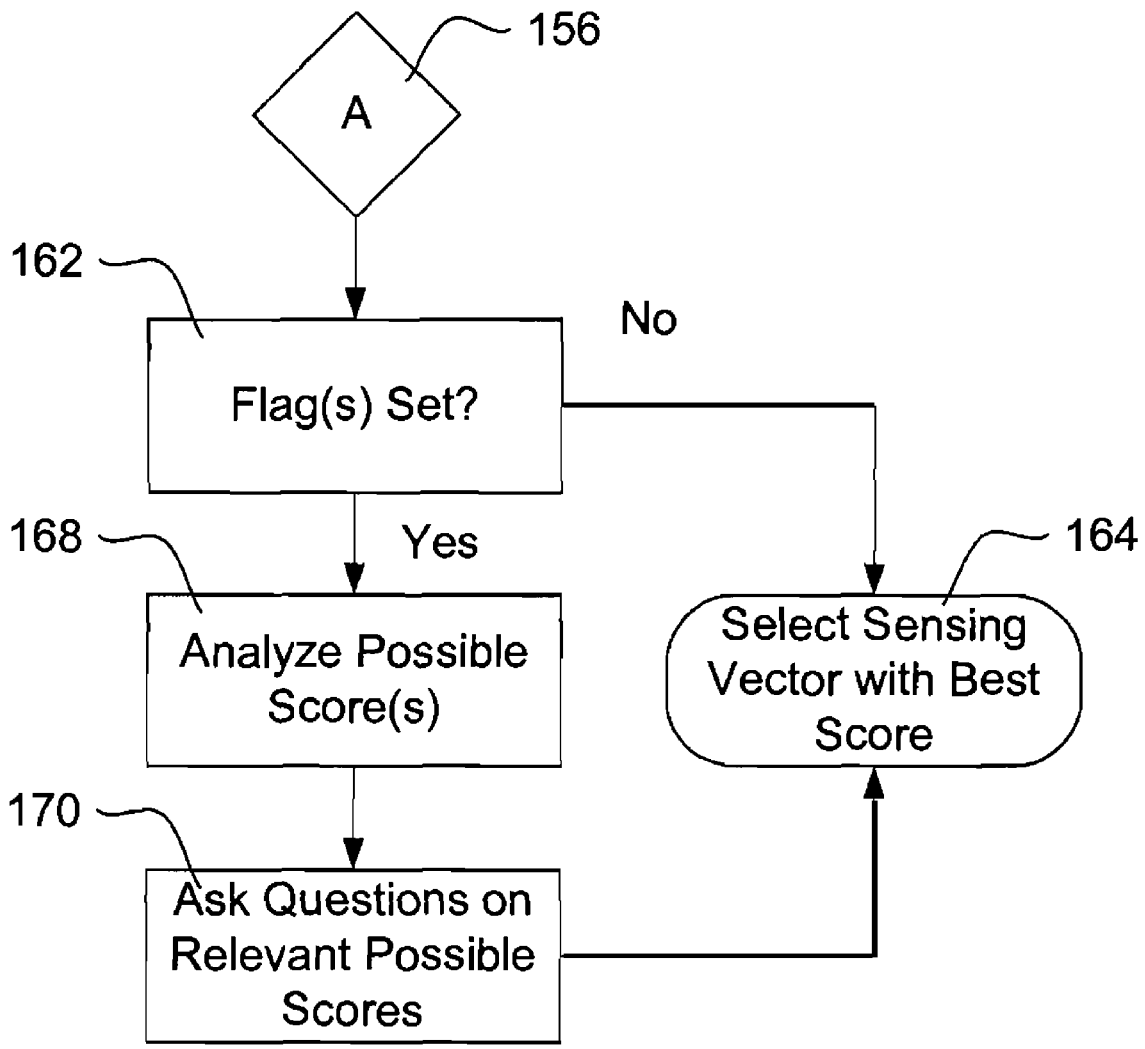

FIGS. 5A-5B illustrate a block diagram for a method of sensing vector analysis. The illustrative method starts at 130. A first vector is analyzed, as shown at 132. The details of analysis are further explained elsewhere. This analysis may include performing the method of FIG. 2, or the thresholds defined in FIG. 2 may be defined prior to performing the method for the first vector or more vectors. The analysis at 132 may provide a Score, as shown at 136, or cannot provide a Score, and instead provides Possible Scores, as shown at 134.

The use of "Score" and "Possible Scores" terms should be explained. In an illustrative example, the vectoring analysis observes parameters of the sensed cardiac signal to determine whether the signal is likely useful for cardiac event detection. In an illustrative example, interval and/or amplitude analysis is used to determine whether "good" detections are occurring. A "good" detection may have a desirable range of signal-to-noise ratio (SNR) and/or amplitude, and may avoid detecting undesired "events" (artifacts). If the analysis indicates regular detections are occurring, and early detections are not occurring, a Score is calculated for the sensing vector. The Score is an example of a metric for the received signal that indicates the quality of the sensing vector for cardiac event detection purposes. In an illustrative embodiment, the Score is calculated by the use of a polynomial including terms relating to the SNR and/or amplitude of captured signal(s).

If the analysis does not, with certainty, parse out noisy detections from actual cardiac event detections, then two or more Possible Scores may be calculated, each based on an assumed resolution of the ambiguity or uncertainty that prevents calculation of a score. For example, two Possible Scores may be calculated, one assuming the QRS peak exceeds the T-wave or other noise peak, and the other assuming the QRS peak does not exceed the T-wave or other noise peak. The following illustrative examples utilize a particular calculation of Scores and Possible Scores for sensing vectors, the details of which may be modified in various suitable ways. It is sufficient that the Score or other metric provide an indication of the quality of the signal captured along a sensing vector for purposes of cardiac event detection and/or analysis.

Returning to the example in FIG. 5A, if the analysis yields only Possible Scores, as indicated at 134, a question flag is set for the first vector, as shown at 138. The question flag indicates that the operator may need to provide input to the vectoring process to determine which of the Possible Scores is the correct Score to use for the first vector by observing whether "QRS>T-wave?". However, rather than immediately asking the operator's assistance, the method instead analyzes the second vector, as shown at 140.

Returning to step 136, if a Score is provided for the first vector, the method next determines whether the Score for the first vector exceeds a predetermined threshold, as shown at 142. In the illustrative method, if the threshold is exceeded, this indicates that the first vector provides excellent sensing, and further analysis is deemed unnecessary. Therefore, if the threshold is exceeded for the first vector, the method ends by selecting the first vector, as indicated at 144. Otherwise, the method goes on to analyze the second vector, as shown at 140.

Steps 142 and 144 represent an early exit condition for the system, which may allow it to terminate vector selection early when a "good" vector is identified. In another embodiment, as discussed below by reference to FIG. 14, early exit conditions may be omitted and/or disabled. The system would then be configured to test each vector before making a selection of one vector over the others. In an illustrative example, a vector with a highest score may be chosen when early exit conditions are disabled or unavailable. In another illustrative example, each vector is analyzed, and vector selection occurs in a preferential manner in which a first "preferred" vector is compared to a threshold in a manner similar to that of steps 142 and 144 after analysis of every vector.

As with the first vector, analysis of the second vector yields either a Score, as indicated at 152, or a Cannot Score and instead provides Possible Scores, as shown at 150. If Possible Scores are provided, the question flag is set for the second vector, as shown at 154. The method then goes to A, as shown at 156, which continues in FIG. 5B.

If analysis of the second vector yields a Score, the method continues from block 152 to determine whether the Score for the second vector exceeds a threshold, as shown at 158. Again, if the threshold is exceeded, this indicates the second vector provides excellent sensing and so the method ends by selecting the second vector, as shown at 160. As before, the early exit conditions of steps 158 and 160 may be disabled or omitted. Otherwise, the method continues to A 156 in FIG. 5B. The steps shown for the first and second vectors may be repeated for any number of vectors, depending upon the particulars of the implantable cardiac stimulus system.

Referring to FIG. 5B, from A 156, the method determines whether any of the question flags have been set, as shown at 162. If not, the method simply selects the sensing vector with the best Score, as shown at 164. If one or more flags have been set, the method continues at 168 by analyzing the Possible Scores. The operator (the attending physician) may be asked questions regarding any of the relevant Scores or Possible Scores.

The analysis at 168 may include determining whether any questions need to be asked. In one embodiment, if any vector yields a Score, no question is asked of the operator. In this way, the operator simply allows the implanted device to select a sensing vector unless input is, in fact, necessary.

In another embodiment, if at least one vector yields a Score, and none of the available Possible Scores from other vectors exceeds all available scores, the operator is not asked any question, since the Possible Scores cannot provide the best available vector. The operator may be asked only relevant questions by selecting the vector having the best Possible Score first. If needed, the operator is asked the question(s), as shown at 170. If the operator answer eliminates the best Possible Score, the method may iterate to ask additional questions relative to one or more next-best Possible Scores. Or, if the answer eliminates the best Possible Score, and the remaining highest score is a Score, rather than a Possible Score, a corresponding sensing vector is selected. Then, the sensing vector with the best Score is selected, as shown at 164.

In yet another embodiment, the implanted device may initiate the vector selection process itself, when it is not in communication with the programmer. This may be the case, for example, if the device determines, during operation, that it cannot accurately observe cardiac activity using a selected vector. If the implanted device initiates vector selection when it is not in contact with a programmer, it cannot request or receive user input. In this instance, if no vector scores can be generated, the device may return to observing with the previously used vector, even though it has been found poorly suited. This circumstance of poor operation may be addressed by some embodiments in which the vectoring method identifies a first, primary or default vector as well as a second, back-up vector, as is further discussed below.

It should be noted with respect to FIGS. 5A-5B that the portion of the method shown in FIG. 5A selects a vector depending on whether the vector provides a sufficient Score. The portion of the method in FIG. 5B, on the other hand, selects the vector with the best Score.

In some embodiments, both first and second sensing vectors are selected, with the first sensing vector being a primary or default sensing vector and the second sensing vector being an alternative or clarifying vector. For example, during a given cardiac episode, if the first vector provides at best ambiguous indications of whether therapy is needed, the second vector may be used to resolve any ambiguity. In other embodiments, a second sensing vector may be identified during the initialization procedure in case, at a later time, the first sensing vector becomes unsuitable (due to changes in physiology, external noise, etc.) or unavailable (due to mechanical failure, for example). For embodiments identifying first and second sensing vectors, the method of FIGS. 5A-5B may simply continue, using similar steps and processes, until a second vector is identified in like fashion. Third and additional vectors may also be identified.

Figure 6:
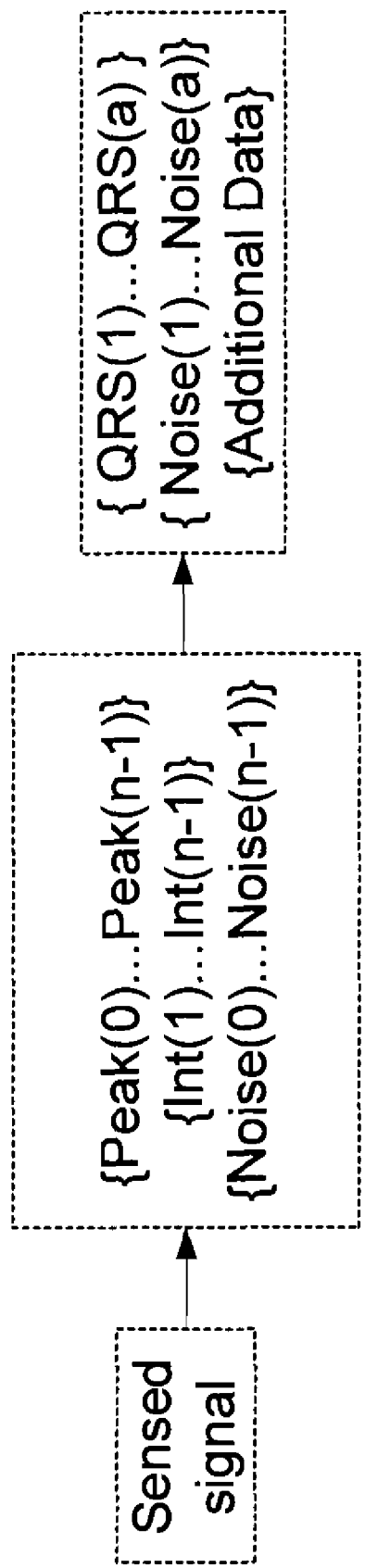
FIG. 6 illustrates a simplified model of an illustrative method.

An illustrative method is shown by FIG. 6. A sensed signal is parsed using detection techniques into various significant features including, for example, peak amplitudes, intervals between peaks, and noise levels between peaks. FIGS. 5A and 5B illustrate an analytical form for this first step. Next, the features identified by the detection techniques are further analyzed to reduce the number of variables under consideration. In the illustrative example of FIG. 6, a set of {n} detected events is analyzed to generate a set of {a} identified QRS peaks and associated noise levels, where the only known relationship between n and a is that n≧a. Because the sensed signal may not readily parse and condense into the data pairs shown, allowance is made for ambiguity during signal processing by carrying forward "additional data" as well. The additional data may include temporal data indicating when detected events occur. If necessary, the implications of the "additional data" may be determined by seeking user input, as further set forth below.

Figure 7A:
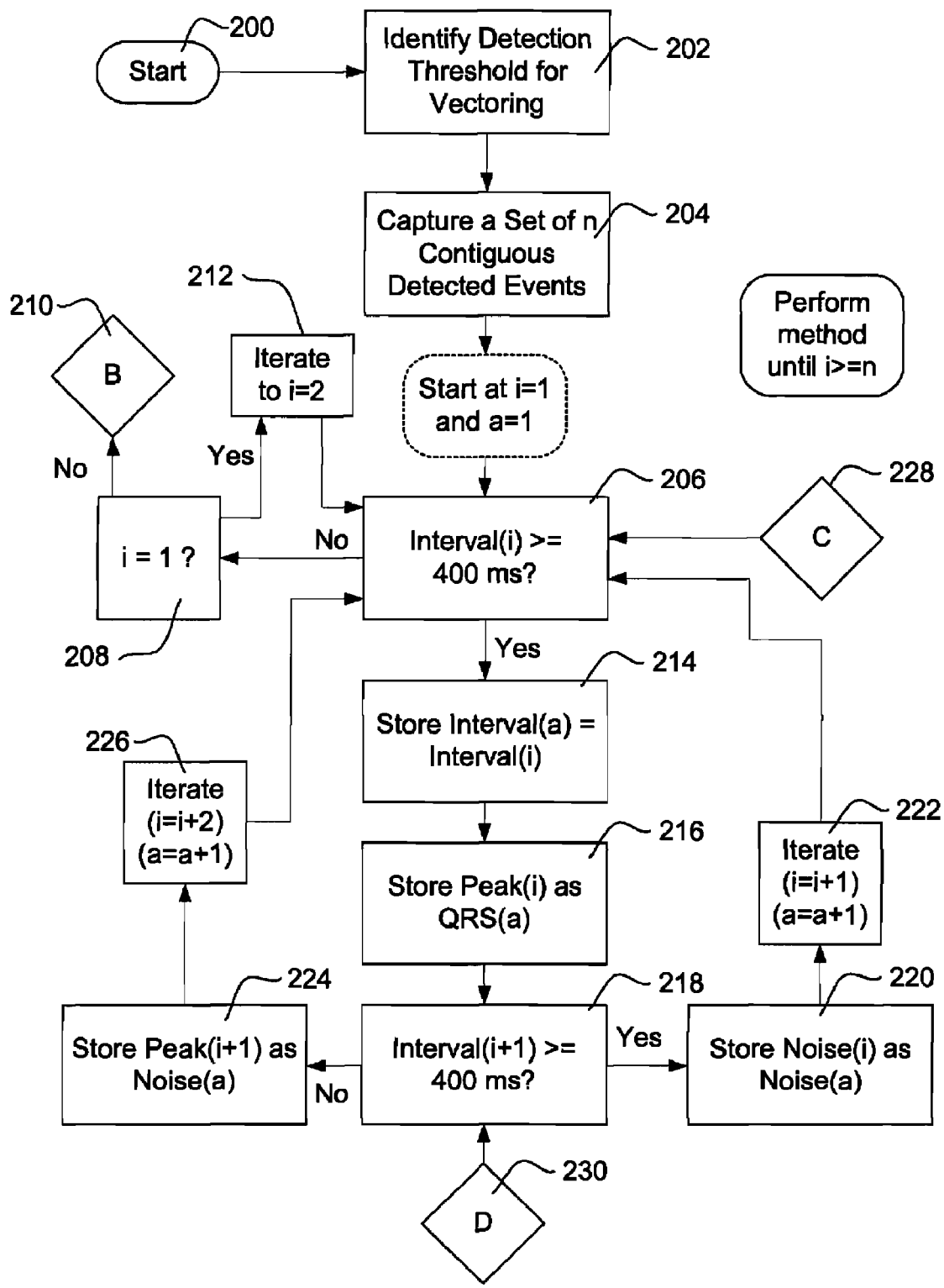
FIGS. 7A-7B illustrate a block diagram for a method of signal analysis within the vector analysis of FIGS. 5A-5B.
Figure 7B:
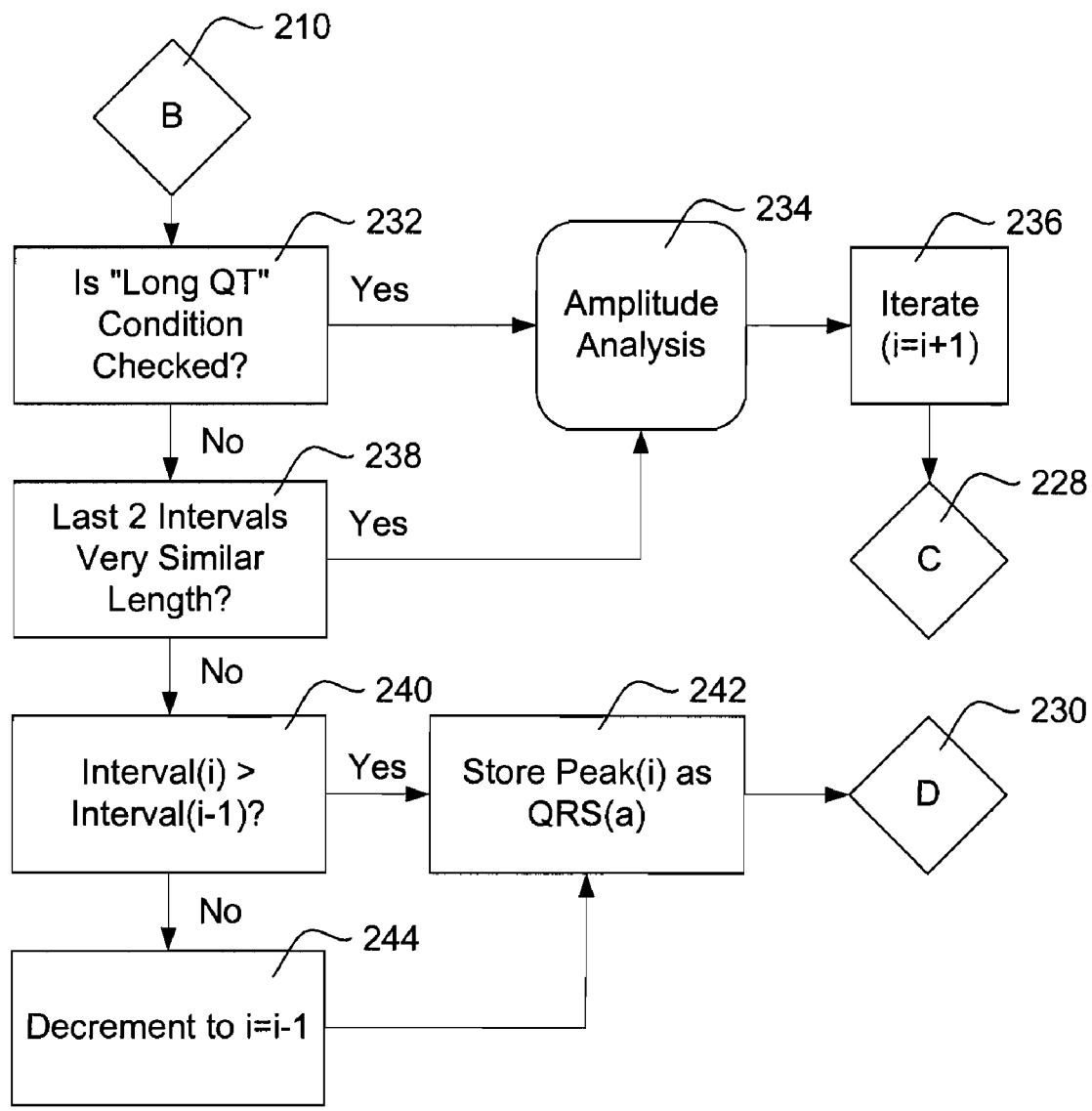

FIGS. 7A-7B illustrate a block diagram for a particular form of the method of FIG. 6. The example illustrated in FIGS. 7A-7B is a particular form for transferring data related to a sensing vector into metrics for evaluating the merits of a given sensing vector against one or more thresholds and/or other sensing vectors. From start block 200, the illustrative method identifies a detection threshold for vectoring, as shown at 202. In some embodiments, step 202 may be achieved by the method of FIG. 2, for example. Next, the illustrative method captures {n} contiguous detected events, as indicated at 204. The "detected events" may occur when the detection threshold is crossed by the sensed signal.

Selected data samples associated with the detected events are also kept for analysis. In an illustrative embodiment, n=11, although other larger or smaller sets of events may also be used. An iterative analysis follows for events marked initially with the i variable, with the iterative method continued until i≧n, although in some embodiments the method may abort if it becomes clear that the vector being considered is unsuitable. For the first iteration, coming from block 204, the illustrative method uses i=1 and also sets another variable a=1.

The loop then starts for the {n} detected events by considering the interval between a first (i−1) event and a second (i) event. As shown at 206, an interval between the $i^{th}$ event and the i−1$^{th}$ event, Interval(i), is compared to a threshold, with 400 milliseconds used for illustrative purposes. If the threshold is not exceeded, the method continues at B, as shown at 210, in FIG. 7B, unless, as indicated at step 208, the first interval was being considered (Interval(1)), in which case the method simply iterates to i=2, as shown at 212, and loops back to step 206 again. If, at 206, the interval is greater than the threshold, then the interval is stored as Interval(a), as shown at 214, and the peak captured during the $i^{th}$ refractory period is stored as QRS(a), as shown at 216.

The interval between i and i+1 (Interval(i+1)) is then considered as shown at 218, and compared to a threshold, which is again shown for illustrative purposes, as 400 milliseconds. If at 218 the threshold is exceeded, then the peak signal captured during CT(i), the continuation time that follows refractory for the $i^{th}$ detection, is stored as Noise(a), as indicated at 220. The method then iterates as shown at 222, and returns to step 206 but with i=i+1 and a=a+1.

Returning to step 218, if the (i+1)$^{th}$ interval considered there does not exceed the threshold, then the refractory peak that caused the latter detection is stored as Noise(a), as shown at 224. This occurs because it is assumed that the latter detection occurred too close to the prior detection to be another QRS complex. The illustrative 400-millisecond threshold interval is used in association with a method that should be performed when the patient's heart rate is in the range of about 30 to 150 beats-per-minute (bpm). Detections occurring with less than a 400-millisecond interval would correspond to a higher beat rate (150 bpm or more), and therefore the method assumes that shorter intervals indicate one or more detections are caused by noise. The method may be tailored to other patient beat rates, if desired.

From 224, the next iteration starts at 226 after another iteration, this time with i=i+2 and a=a+1. The i variable receives a double iteration since, as shown at 224, the (i+1)$^{th}$ peak is considered to be noise. When returning to step 206, in some embodiments the next interval is taken from i−2 to i, spanning the i−i event that has been identified as likely occurring due to noise. For example, at a microcontroller level, a flag may be set to indicate double iteration at step 226, with the flag being reset once the interval is considered in step 206.

Turning now to FIG. 7B, the method picks up at block B 210, which continues from block B 210 in FIG. 7A. As shown at 232, the method continues by determining whether a "Long QT" condition has been checked. In an illustrative embodiment, the "Long QT" condition allows an operator to indicate to the implantable device system and/or the programmer that the patient is susceptible to a long interval between the Q and T signals. For such a patient, the T-wave is likely to occur rather late after the R-wave in the overall cardiac cycle. By reference to the analysis using a refractory period and CT interval, as shown in FIG. 3A-3B, a "Long QT" patient may experience the T-wave after expiration of the CT interval. This may cause the detection circuitry to detect a threshold crossing due to the T-wave artifact after the CT time period expires in one or more sensing vectors.

If the "Long QT" condition is checked, the method continues with amplitude analysis, as indicated at 234. An illustrative method of amplitude analysis 234 is further explained below by reference to FIGS. 8 and 9A-9C. After amplitude analysis at 234, the method iterates using i=i+1, and returns to block C 228 in FIG. 7A, which ultimately sends analysis to block 206. It should be noted that the {a} variable is not iterated here, as the data elements QRS(a) and Noise(a) have not been filled with data during amplitude analysis at 234.

If the "Long QT" condition is not checked at block 232, the method determines whether Interval(i−1) and Interval(i) are very similar in length. In an illustrative example, the intervals are considered to be very similar in length when their durations are within 50 milliseconds of one another, for example, 300 milliseconds is considered very similar in length to 320 milliseconds, although the exact parameters for determining similarity may vary. If the intervals are very similar in length at 238, the method continues with amplitude analysis, as shown at 234, as before.

If the intervals compared at 238 are not similar, the method determines whether Interval(i) is longer than Interval(i−1), as shown at 240. If so, then Peak(i) is stored as QRS(a), as shown at 242. Otherwise, if Interval(i−1) is not shorter than Interval (i), the method decrements the {i} variable to i=i−1, as indicated at 244, and continues to step 242. Using either course, the method continues from step 242 to D, as shown at 230, which returns to FIG. 7A, directing the method to step 218.

Figure 8:
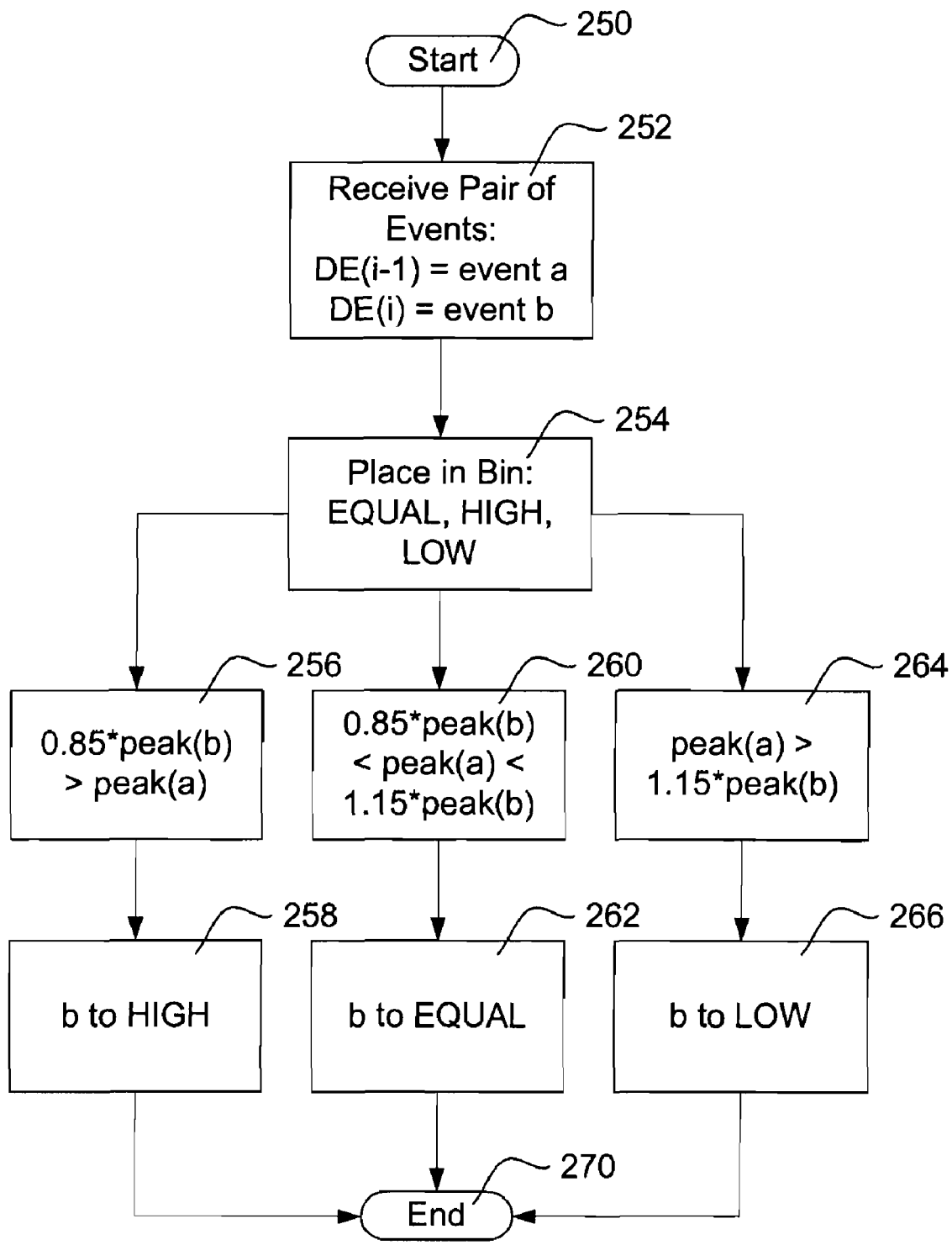
FIG. 8 illustrates a block diagram for a method of assessing cardiac signal quality.

Detected events that are analyzed in FIGS. 7A-7B and found to be QRS events are placed in a QRS bin, while events that are found to be noise are placed in a Noise bin. Those events that undergo amplitude analysis are placed in bins as illustrated in FIG. 8. In some embodiments, the method may be aborted if too many events are placed in bins for amplitude analysis, although this is not necessarily the case.

FIG. 8 illustrates a block diagram for a method of assessing cardiac signal quality. This method may be a part of the amplitude analysis 234 shown in FIG. 7B. From start block 250, the method receives a pair of events a and b, as shown at 252. Event b is to be placed in one of several bins, as indicated at 254, depending upon the relative amplitudes of events a and b. More particularly, if the amplitudes of peaks a and b are more or less equal, within +/−15% margin, event b is placed in the EQUAL bin, as shown at 260, 262. If peak b is larger than peak a, outside of the margin for the two being equal, then b is placed in the HIGH bin, as shown at 256, 258. Conversely, if peak a is much greater than peak b, then b is placed in the LOW bin, as shown at 264, 266. The binning process of FIG. 8 is used later in FIGS. 9A-9C.

Figure 9A:
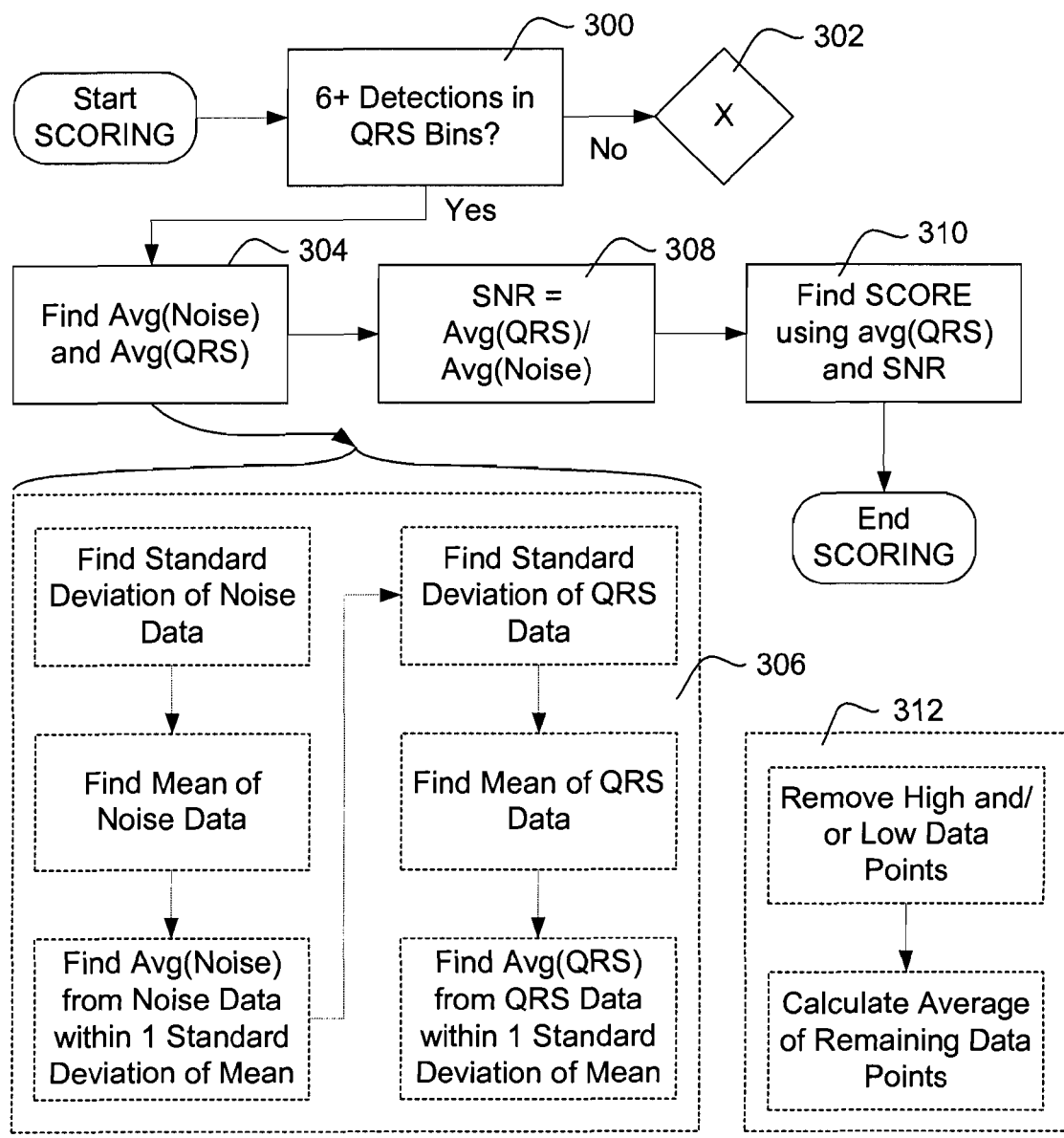
FIGS. 9A-9C illustrate a block diagram for a method of analyzing a cardiac signal.
Figure 9B:
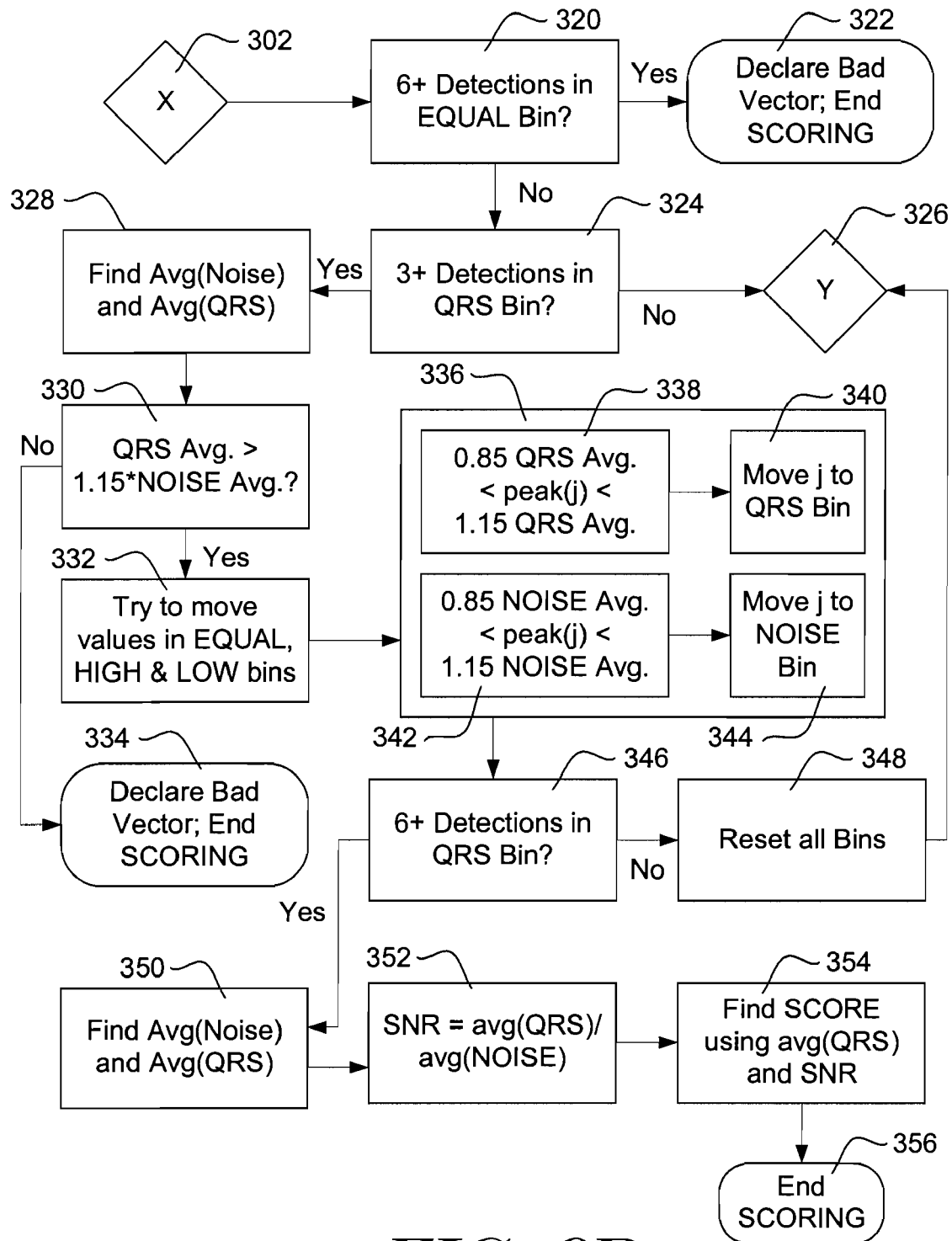
Figure 9C:
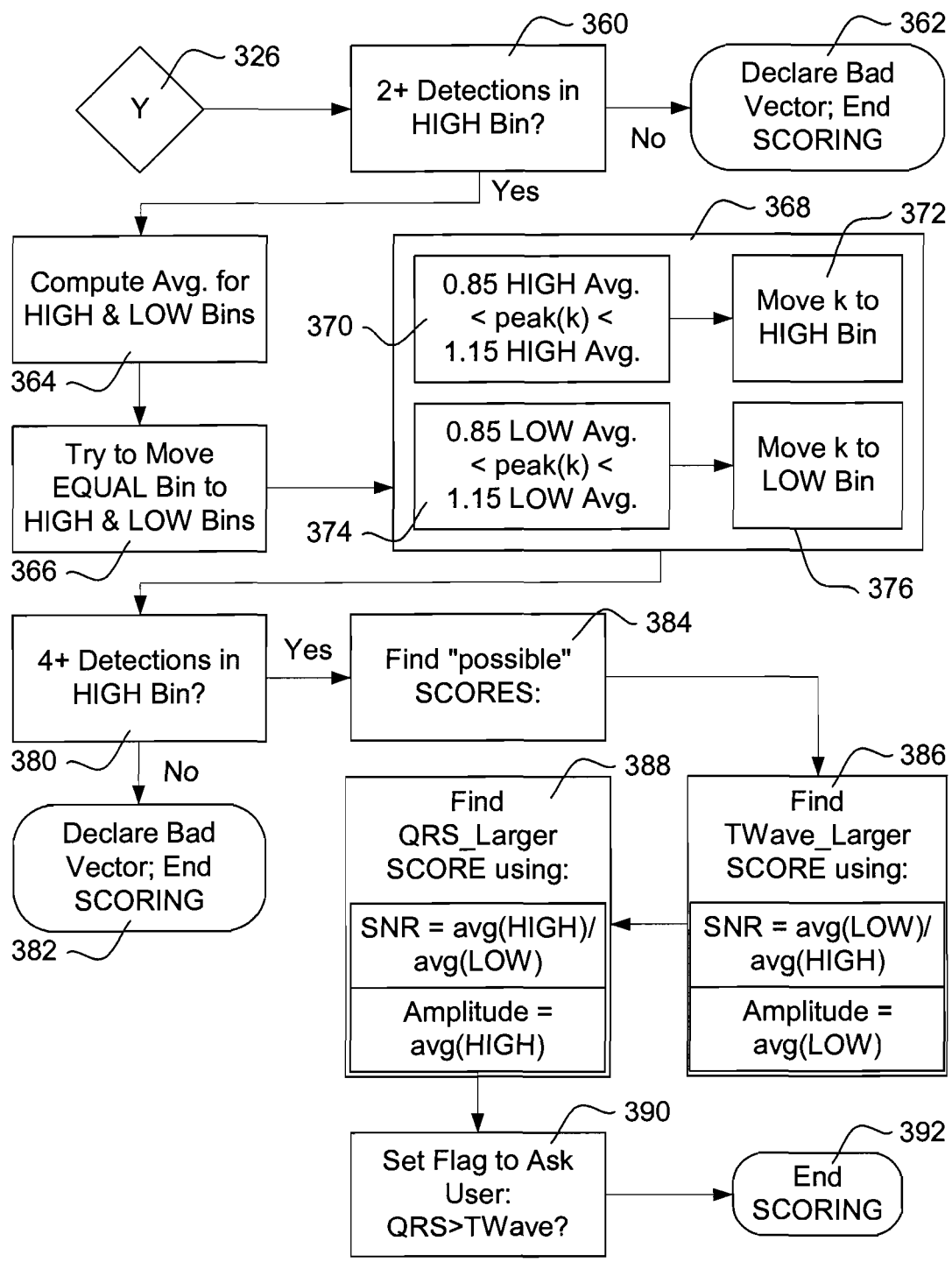

FIGS. 9A-9C illustrate a block diagram for a method of analyzing a cardiac signal. The method of FIGS. 9A-9C is a method for calculating a Score for a given vector. The method assumes the use of the methods of FIGS. 7A-7B to analyze {n} contiguous detected events. These events, as explained above, may generate paired Noise and QRS data elements, which are separated and placed in a QRS bin and a NOISE bin. Also, with the amplitude analysis of FIG. 8, some events related to ambiguous intervals may be placed in bins for HIGH, LOW and EQUAL.

For illustrative purposes, the example of FIGS. 9A-9C uses n=11 as the number of initially detected events. In other embodiments, any suitable number of events may be used. The parameters used in the following example are merely illustrative of one manner of performing the method, and may be modified to suit other systems, specific circumstances, or variables. The method of FIGS. 9A-9C begins at a start block, and determines whether 6 or more of the n=11 detections have been placed into the QRS bins, as shown at 300. If not, the method continues with block X 302 in FIG. 9B. This condition may also be a condition in which a set of detections are considered and, if more than half of the detections are in the QRS bins, the condition at 300 is met.

If there are 6 or more detections in the QRS bin, then the average amplitudes for noise and QRS bins are calculated, as shown at 304. An illustrative method of performing this calculation is shown in block 306. The standard deviation is determined for the noise data, as well as the mean. Then the average is calculated by excluding any outlying data (illustratively, data that falls outside of one standard deviation of the mean). The process is repeated for the QRS data as well. Alternatively, the method shown in block 312 may be used instead to calculate averages for one or both of Noise and QRS data. In this somewhat simpler method, a highest data point and/or a lowest data point are removed from the data set and the average is calculated using the reduced data set, as shown at 312.

The SNR is then calculated as the ratio of the average amplitude of the remaining events in the QRS bin to the average of the amplitudes stored in the NOISE bin, as shown at 308. Next, the SCORE is calculated using the average amplitude of the remaining events in the QRS bin along with the SNR, as shown at 310.

Next, a value for use in scoring based on the average QRS amplitude ($QRS_{Avg}$). In an illustrative example, the following general polynomial formula is used:

$$S_A = GAIN * \frac{\exp(N1 * [\ln(N2 * QRS_{Avg} - N3)]^2)}{D1 * QRS_{Avg} - D2}$$

Where:

GAIN = 64.0   $N1 = -34.7222$
$N2 = 0.2326$   $N3 = -0.6047$
$D1 = 0.3008$   $D2 = -0.7821$

It should be noted that the limits for $QRS_{Avg}$, in this illustrative embodiment, are $0 < QRS_{Avg} < 4.0$. A graph illustrating the relationship between $S_A$ and $QRS_{Avg}$ is shown in FIG. 10A.

The illustrative Scoring method further includes calculating a value $S_R$ as:

$$S_R = C_R * (SNR)^2$$

Where:
 if $SNR \leq 3.5$, $C_R = 0.1$;
 if $3.5 < SNR \leq 10$, $C_R = 1$; and
 if $SNR > 10$, $S_R = 100$ It should be noted that the variable $S_R$ is given a constant value when the SNR is greater than 10, at least in part to avoid over-contribution of large SNR to the final Score calculation. A graph illustrating the relationship of $S_R$ to SNR is shown in FIG. 10B.

In some embodiments, the dynamic range of the analysis system for use in association with the vector under consideration may be identified depending upon the average value found and/or the mean of the QRS data. For example, the method may include selecting a dynamic range for the analog-to-digital converter, incoming signal amplifier, or other component(s) of the system. In an illustrative example, a higher order polynomial in one variable (i.e. in $QRS_{Avg}$) is used to find the score as follows:

$$S_A = \{C_1 * (QRS_{Avg})^6 + C_2 * (QRS_{Avg})^5 + C_3 * (QRS_{Avg})^4 +$$
$$C_4 * (QRS_{Avg})^3 + C_5 * (QRS_{Avg})^2 + C_6 * (QRS_{Avg}) + C_7\}$$

-continued

Where, if $QRS_{Avg} \leq 2.0$, $C_1 = 22.5718$   $C_2 = -105.9666$   $C_3 = 160.2345$
$C_4 = -88.9262$   $C_5 = 29.6019$   $C_6 = -1.2859$
$C_7 = 0.0087$ And, if $QRS_{Avg} > 2.0$, $C_1 = 56.5544$   $C_2 = -1069.9959$   $C_3 = 8310.0056$
$C_4 = -33849.9682$   $C_5 = 76139.7271$   $C_6 = -89551.3405$
$C_7 = 43035.7880$ The illustrative method utilizing these coefficients is adapted for use in a system in which the electronics that receive the patient's cardiac signals can have a first dynamic range of up to 2.0 millivolts and a second dynamic range of up to 4 millivolts. With such a system, peak amplitudes for the QRS in the 1.7-2.0 millivolt range create a likelihood of clipping and/or difficulty in using only one of the two dynamic ranges all the time. Likewise, peak amplitudes in the range of 3.5-4.0 millivolts create a likelihood of clipping as well, making this a less preferred range.

Figure 10C:
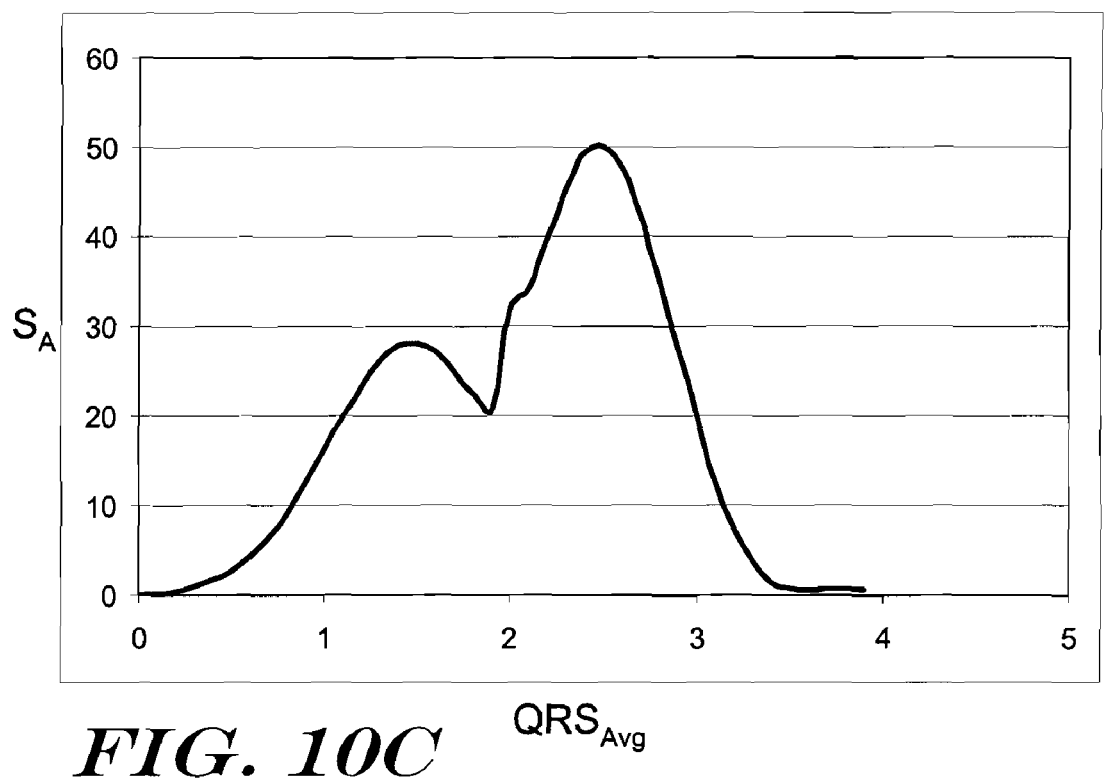

A graph comparing $S_A$ to $QRS_{Avg}$ with this sixth-order polynomial formula is shown in FIG. 10C, and it can be seen that $S_A$ is given first and second peaks, with a dip in the region where $QRS_{Avg}$ is about 1.7-2.0 volts. The above illustrates use of a general polynomial (using series functions such as the exponential and natural logarithm) as well as use of an $n^{th}$ order, non-continuous polynomial. These formulae are merely illustrative, and other polynomial forms may also be used. Further, as shown by the embodiment of FIG. 10A, there is no need to specially configure the system for input electronics having adjustable or multiple dynamic ranges, unless so desired.

Next, the Score is determined from:

$$S_A * S_R = Score$$

Referring again to FIG. 9A, with the Score calculated at 310, scoring is complete, and the method ends.

Turning now to FIG. 9B, the method picks up at block X 302, coming from FIG. 9A. The method determines whether there are 6 or more (again, out of 11, although these numbers may be varied) detections in the EQUAL bin, as indicated at 320. If so, the sensing vector under consideration is yielding too many ambiguous results and too much noise, causing overdetection that the system has a difficult time resolving. Therefore, the sensing vector is declared bad, as shown at 322, and the scoring method ends as no Score can be returned for the vector under consideration. The overall vectoring method would, at this point, continue analysis with a different sensing vector or, if all vectors have been analyzed, proceed to select the best vector among those not declared bad vectors.

If the condition at 320 is not true, then it is determined whether there are at least 3 (of 11) detections in the QRS bin, as indicated at 324. If not, the method continues at block Y 326 and on to FIG. 9C. If there are 3 or more detections in the QRS bin, the method continues at 328, where the Average for NOISE and QRS are each calculated. This may be performed in accordance with one of the methods of blocks 306 or 312 of FIG. 9A, although due to the reduced data set initially under consideration, the method of block 312 may be more useful, as the statistical analysis of block 306 is less useful.

Next, the QRS Average and NOISE Average are compared to one another to verify that the bins contain values that are separated from one another, as shown at 330. The use of 1.15 as a multiplier is merely illustrative of one form of this comparison. In another embodiment, rather than a multiplier, an offset having a stable value is used, or a formula such as Ax+B may be used, with A as a multiplier and B as an offset. Other comparisons may also be made to determine separation. If the values in the QRS and NOISE bins are too close to one another, the method jumps to step 334, where a bad vector is declared and scoring ends.

If the condition at 330 is met, the remaining values in the EQUAL, HIGH and LOW bins are analyzed to see which, if any, can be moved to one of the QRS or NOISE bins, as indicated at 332. The data points in the EQUAL, HIGH and LOW bins are moved to QRS and/or NOISE by the method steps shown in block 336. For each data point, j, the peak amplitude is compared to see if it may fit in one or the other of the QRS or NOISE bins due to its amplitude similarity, using a +/−15% margin to determine similarity. The margin used may vary in other embodiments. If the data point, j, is sufficiently similar to the average of either the QRS or NOISE bin, it is then moved to that bin. Steps that move j to the QRS bin are shown at 338, 340, and steps that move j to the NOISE bin are shown at 342, 344.

After each data point in the EQUAL, HIGH and LOW bins has been considered in block 336, it is again determined whether there are 6 or more detections in the QRS bin, as indicated at 346. If so, the Averages for the NOISE and QRS bins are recalculated, as indicated at 350, for example, by the method of one of blocks 306 or 312 in FIG. 9A. Next, the SNR is determined as shown at 352, and a score is calculated as shown at 354. Once the Score is found at 354, the scoring method ends, as noted at 356.

If the condition at 346 fails, and there are still less than 6 detections in the QRS bin after block 338, the QRS, NOISE, HIGH, EQUAL and LOW bins may be reset to their original status prior to steps 336-344, as shown at 348. The method then goes to block Y 326, and continues in FIG. 9C.

Turning to FIG. 9C, the method continues from block Y 326. It is determined whether there are 2 or more detections in the HIGH bin, as indicated at 360. If not, then a bad vector is declared, as indicated at 362, and the scoring method ends because a score cannot be returned for the vector under consideration.

If there are at least 2 detections in the HIGH bin, the method goes from block 360 to 364, where the average amplitudes for the data points in the HIGH and LOW bins are computed. This may be performed using a method similar to those shown in one of blocks 306 or 312 in FIG. 9A or, instead, because the data set under consideration is already limited, the full set of data points in each bin may be used to calculate averages in step 364.

The next step is to attempt to move points from the EQUAL bin into the HIGH and LOW bins, as shown at 366. This is performed as indicated in block 368. For each data point k in the EQUAL bin, the amplitude stored for that data point is compared to the average for the HIGH bin, as shown at 370, to determine if it is similar to the average for the high bin, within a defined margin of +/−15%. If so, then the data point k is moved to the HIGH bin, as shown at 372. Otherwise, the amplitude for k is compared to the average for the LOW bin, again with a margin of +/−15%, as shown at 374. If the amplitudes are similar, k is moved to the LOW bin, as indicated at 376. These steps are repeated for each point k in the EQUAL bin.

In some embodiments, the steps in block 368 are performed such that the test at 370 is performed first, and if it fails, then the test at 374 follows. For example, in the context of programmer code, one of the comparisons will appear first and will therefore occur first. In this manner, overlap of the +/−15% margin around the HIGH and LOW averages does not create ambiguity, as each peak(k) can only be moved into one bin or the other. The same may be true for Block 336 in FIG. 9B.

After block 368 is completed, the method determines whether 4 or more detections are in the HIGH bin, as indicated at 380. If not, then a bad vector is declared as shown at 382, because no score can be returned. If there are 4 or more points in the HIGH bin, then possible scores are determined, as indicated by 384.

As shown in block 386, a TWave_Larger Score is calculated. This Possible Score assumes that the T-wave will have a greater amplitude than the QRS signal. Therefore, it assumes that the detections in the HIGH bin represent T-waves, while the detections in the LOW bin represent QRS signals. Therefore the SNR is calculated as the ratio of the average amplitude in the LOW bin to the average amplitude for the HIGH bin. This may be performed using the full data sets in each of the LOW bin and HIGH bin, or the data sets may be reduced by methods such as shown in blocks 306 and 312 in FIG. 9A. The variable "Amplitude" is then set as the average amplitude for the LOW bin (again, a full or reduced data set may be used to calculate the average amplitude for the LOW bin) as well. The Possible Score is determined as before by the use of the look-up table or chart, although again, other methods could also be used.

Next, as shown at 388, a QRS_Larger Score is calculated. This Possible Score assumes that the QRS signal will have a greater amplitude than the T-wave. Therefore, it assumes that the detections in the HIGH bin represent QRS signals, and the detections in the LOW bin represent T-waves. The SNR is calculated as the ratio of the average amplitude in the HIGH bin to the average amplitude in the LOW bin in similar fashion to that used in block 386, and the amplitude is calculated as the average amplitude for the HIGH bin, again using either full or reduced data sets. The Possible Score is then calculated as before.

After the creation of the Possible Scores (QRS_Larger SCORE and TWave_Larger Score) in steps 386, 388, a flag is set for asking the operator whether "QRS>TWave?" as indicated at 390. If necessary, i.e. if the largest available score is one of the possible scores, the operator can then provide an input that indicates which of the possible scores is correct. With the flag set at 390, the Scoring method ends as indicated at 392 by returning the two possible scores with the flag set.

Figure 11A:
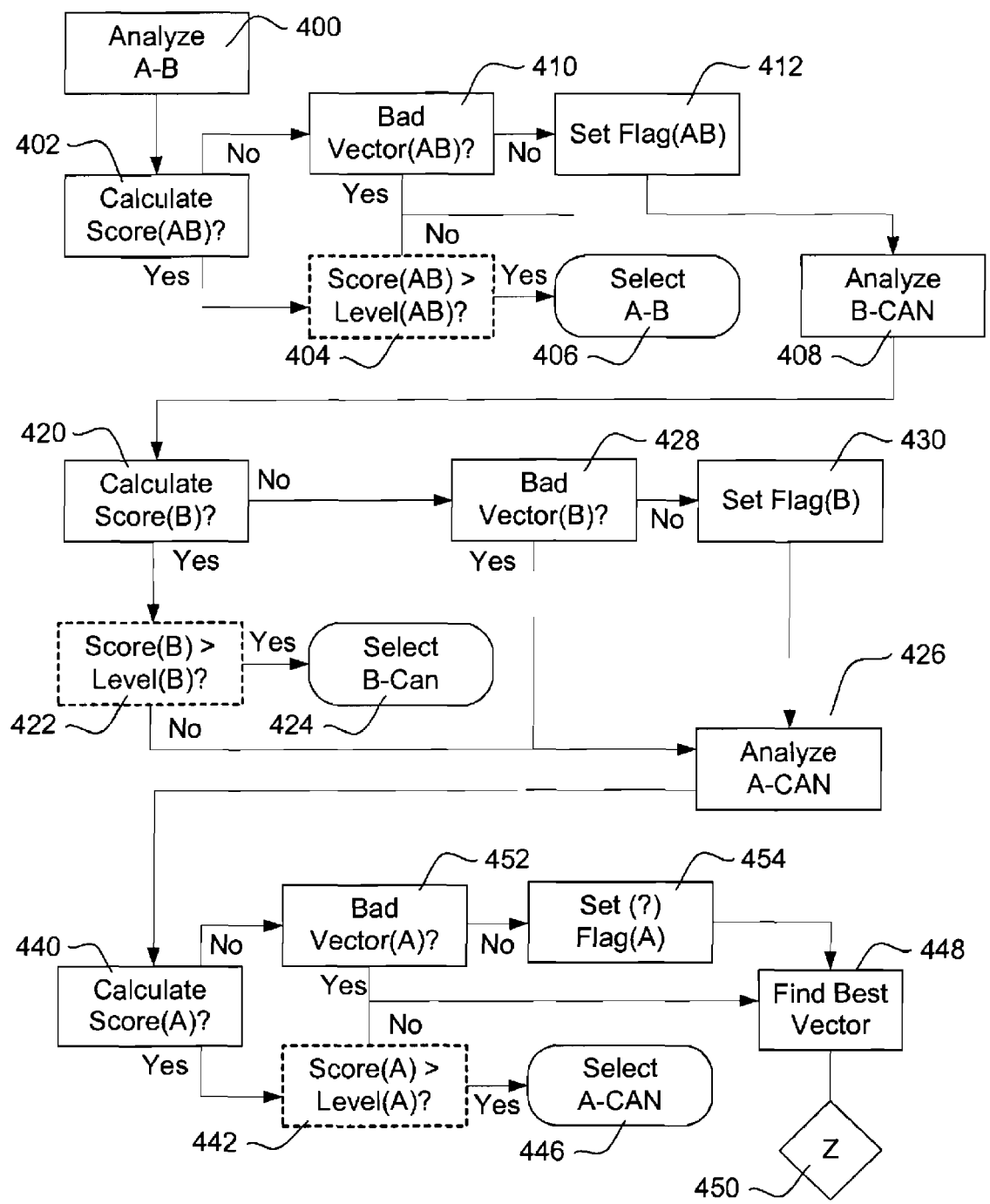
FIGS. 11A-11B illustrate a block diagram for a method of signal vector analysis.
Figure 11B:
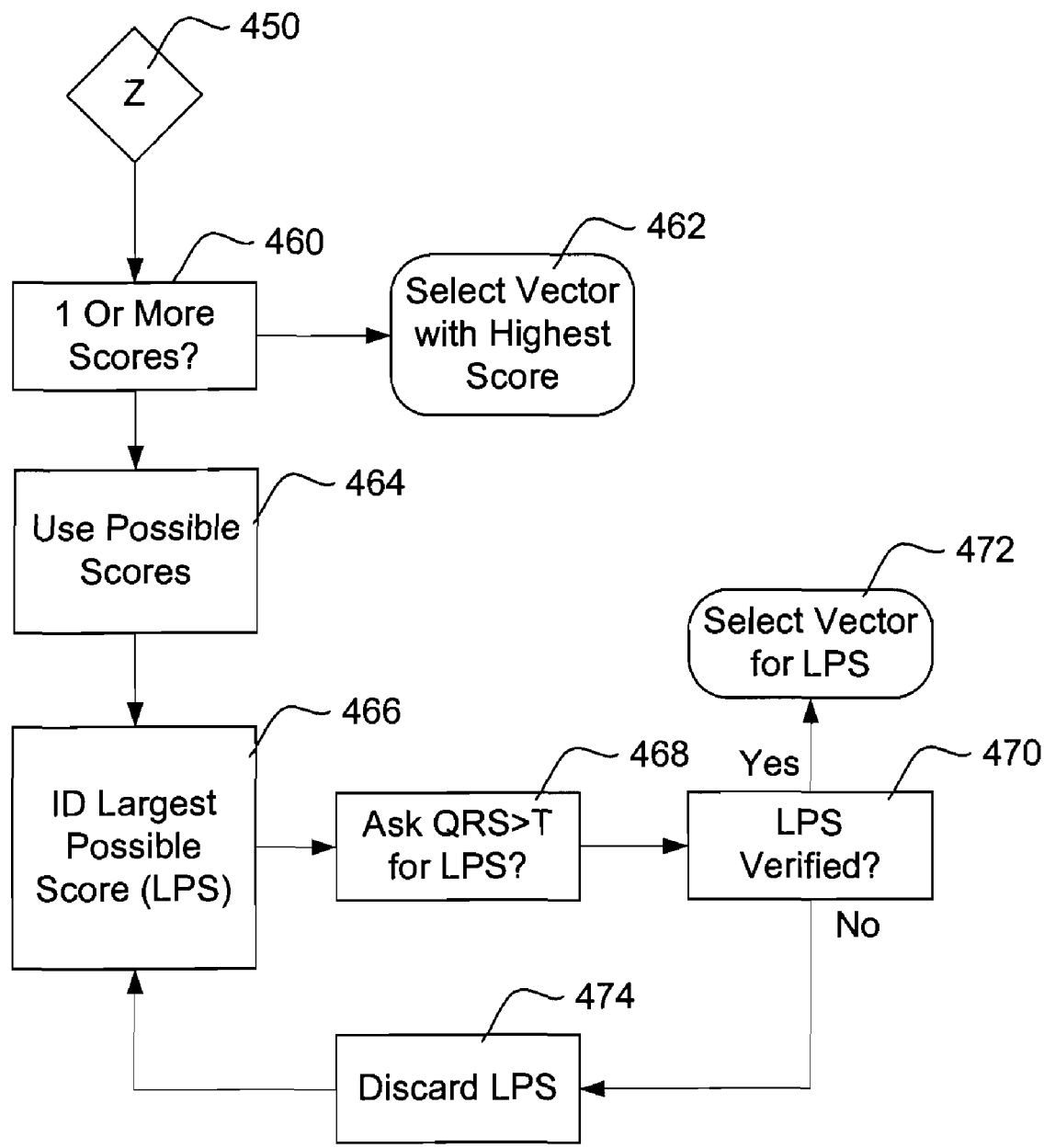

FIGS. 11A-11B illustrate a block diagram for a method of signal vector analysis. The method assumes a system as illustrated in one of FIGS. 1A-1B, with three sensing vectors available: A-Can, B-Can, and A-B. The illustrative vectoring method of FIGS. 11A-11B displays a preference for the A-B vector, then the B-Can vector, and a lowest preference for the A-Can vector. This is not necessary to the practice of the invention, but FIGS. 11A-11B illustrate how such preferences can be incorporated into a vectoring method.

The method begins at block 400, where the sensing vector A-B is analyzed. As shown at 402, the first query is whether a Score(AB) (a Score for the A-B sensing vector) has been calculated during the analysis 400. If so, the method continues at 404 where the generated Score(AB) is compared to Level(AB), a threshold for the A-B sensing vector. If Score (AB) exceeds Level(AB), then the method selects the A-B sensing vector, as indicated at 406, which ends the vectoring method if only one sensing vector is sought. If multiple sensing vectors are sought, then the method may continue by analyzing the other available vectors to select a secondary vector, if desired. In an alternative illustrative embodiment, the early exit condition of steps 404 and 406 may be omitted or, at the user's option, disabled, as shown below in the method illustrated in FIG. 14; early exit conditions are shown throughout the method of FIGS. 1A-11B, although these may be omitted in select embodiments. For this reason, the optional early exit steps 404, 422 and 442 are shown in a different line weight and style in FIG. 11A.

If Score(AB) does not exceed Level(AB), in step 404 (or if step 404 is omitted or disabled), then the method goes to block 408, where the B-Can sensing vector is analyzed. Going back to block 402, if a Score cannot be calculated for the A-B sensing vector, it is determined at 410 whether the A-B sensing vector is a bad vector, as indicated at 410. If so, the A-B sensing vector may be marked as bad, and the method jumps ahead to step 408. Otherwise, the method continues to block 412, where the flag for indicating that operator input is needed relative to the A-B sensing vector is set. With analysis of the A-B sensing vector complete, the method continues to block 408 where the B-can sensing vector is analyzed.

From block 408, it is again determined whether a Score(B) (a Score for the B-Can sensing vector) can be calculated, as shown at 420. If so, the method determines whether the Score (B) is greater than Level(B), a threshold for the B-Can sensing vector, as shown at 422. If Level(B) is exceeded, the B-Can sensing vector is determined to be sufficient for detection use and the method ends (if only one sensing vector is sought) by selecting the B-Can sensing vector, as indicated at 424. If Level(B) is not exceeded, the method continues to step 426, further explained below.

If no Score(B) is calculated, the method determines whether the B-Can sensing vector is a bad vector, as indicated at 428. If so, the B-Can sensing vector may be marked as bad, and the method again continues at step 426. If the B-Can sensing vector is not a bad vector at 428, the method sets a flag indicating that operator input is needed to finish analysis of the B-Can vector to generate a Score, as indicated at 430. Again, the method continues to step 426.

At step 426, the A-Can vector is to be analyzed. It is determined whether a Score(A) (the Score for sensing vector A-Can) can be calculated, as indicated at 440. If so, then it is determined whether Score(A) is greater than Level(A), a threshold defined for the A-Can sensing vector, as shown at 442. If so, then the A-Can sensing vector is selected, as shown at 446. If Level(A) is not exceeded, the method goes to step 448 to find the best vector, which leads to block Z 450 in FIG. 11B.

If Score(A) cannot be calculated at step 440, the method continues to step 452, where it is determined whether the A-Can sensing vector is a bad vector. If so, the A-Can sensing vector may be marked as a bad vector and the method continues to 448 and to block Z 450 in FIG. 11B. If the A-Can sensing vector is not a bad vector, the method continues to step 454 and sets the flag to indicate that operator input is needed to resolve an ambiguity with the A-Can sensing vector. The method then continues to step 448 and on to block Z 450 in FIG. 11B.

In an illustrative example, one of the scoring formats set forth above is used. In this illustrative example, Level(A)=Level(B)=Level(AB)=1750. However, it should be clear to those of skill in the art that the specifics of the scoring formula may be modified, as well as the specifics of the threshold levels used in analysis. In broader form, the illustrative example is one in which several vectors are analyzed in turn to determine whether any can be characterized as "very well suited" to performing cardiac signal analysis and, if not, the most suitable of the vectors is selected.

In another illustrative example, the step of establishing a score has two main phases: first, determining whether the captured signal is amenable to a scoring method, and second, determining whether the captured signal indicates a good sensing vector by calculating a score taking into account identifiable features of the captured signal including identifiable cardiac events and identifiable noise. The first phase takes into account the difficulty in implantable devices of segregating noise from cardiac signal, while the second phase takes into account whether the signal, once segregated, is likely to assist in unambiguous analysis.

Turning to FIG. 11B, the method continues from block Z 450 to step 460, where it is determined whether there are one or more Scores already calculated. If so, the method continues to step 462 wherein the vector with the highest Score is selected. In this manner, the Operator is not asked any questions if at least one vector yields a Score.

If the condition at step 460 fails, the method continues to step 464, where the Possible Scores are used. From the Possible Scores, a largest possible score (LPS) is identified, as shown at 466. Next, the operator is asked whether QRS>T for the sensing vector that corresponds to the LPS, as indicated at 468. The answer given by the operator can either verify or reject the LPS, depending upon whether the calculation resulting in the LPS corresponds to the answer given by the operator.

For example, if the LPS is the QRS_Larger Score for the A-Can sensing vector, the operator will be asked whether, for the A-Can sensing vector, QRS>Twave? If the operator indicates "Yes", then the operator's answer verifies the QRS_Larger Score for the A-Can sensing vector, and therefore the LPS would be verified. If, instead, the operator's answer is No, then the TWave_Larger Score for the A-Can sensing vector would be verified, and the QRS_Larger Score would be discarded because the operator's answer indicates it is an incorrect calculation.

As indicated at 470, the method next determines whether the LPS is verified by the operator's response to the question at 468. If so, then the sensing vector corresponding to the LPS is selected, as indicated at 472. Otherwise, the LPS is discarded, as indicated at 474, and the method returns to step 466. If other possible scores remain, steps 466, 468 and 470 are repeated for one or more additional vectors until step 472 is reached. It should be noted that once a Possible Score is discarded at step 474, the corresponding "other" Possible Score for that vector remains available, however, this "other" Possible Score will be quite low such that, if other available Possible Scores remain, a different vector is likely to offer better sensing. In some embodiments, if the higher Possible Score for a vector assumes a different answer to the "QRS>T" query than is given by the Operator, the vector is found to be a bad vector.

Figure 12:
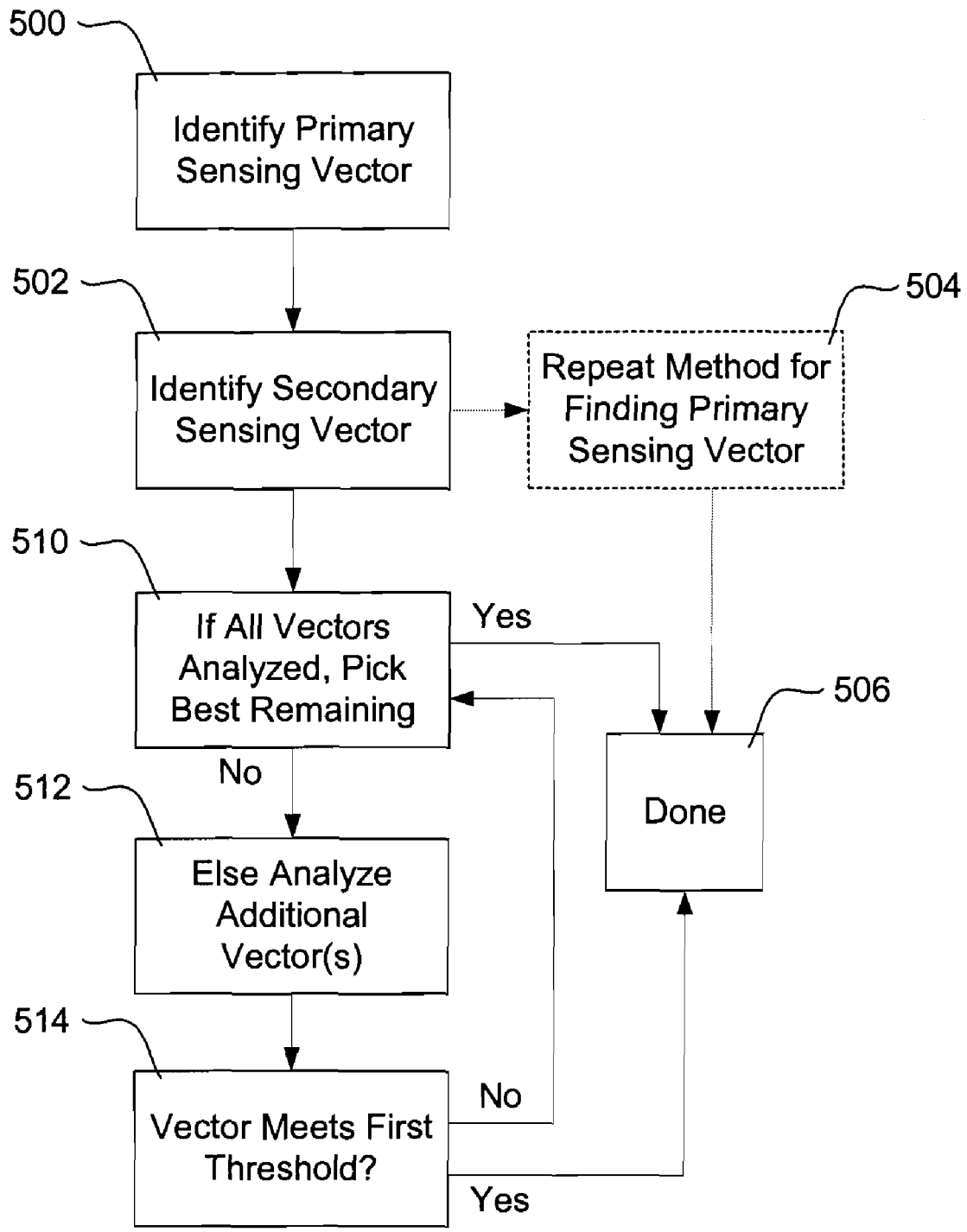
FIG. 12 is a block diagram illustrating a method in which a primary sensing vector and a secondary sensing vector are selected for use in detecting and analyzing cardiac events.

FIG. 12 is a block diagram illustrating a method in which a primary sensing vector and a secondary sensing vector are selected for use in detecting and analyzing cardiac events. As shown at 500, the method first identifies a primary sensing vector. This may be performed, for example, using the methods discussed above.

Next, the method includes identifying a secondary sensing vector, as shown at 502. This may be performed in more than one fashion. For example, as shown at 504, the method used to find the primary sensing vector may be repeated in its entirety, with the method ending at 506. In another embodiment, the method simply continues analysis after identifying the primary sensing vector. As shown at 510, if all of the available sensing vectors have already been analyzed, the method picks the best one and, again, ends at 506.

If not all vectors have been analyzed, then an additional vector is analyzed as shown at 512. If this additional vector meets a first threshold at step 514, illustrating that the additional vector is well suited to cardiac signal analysis, then the additional vector is selected as the secondary vector, and the method ends at 506. In another embodiment, a flag is set if not all vectors have been analyzed at 510, and an additional step is performed at the end of the method to compare the score for the primary vector to the score for the secondary vector. If the secondary vector has a higher score than the primary vector, their designations may be reversed.

If the additional vector does not meet the first threshold at step 514, the method loops back to step 510. The loop continues until either a newly analyzed vector exceeds the threshold at step 514, or all vectors have been analyzed and the best one is selected at step 510. The use of primary and secondary vectors may take several forms, such as those discussed in U.S. patent application Ser. No. 10/901,258, filed Jul. 27, 2004, now U.S. Pat. No. 7,392,085 and titled MULTIPLE ELECTRODE VECTORS FOR IMPLANTABLE CARDIAC TREATMENT DEVICES, the disclosure of which is incorporated herein by reference.

Figure 13:
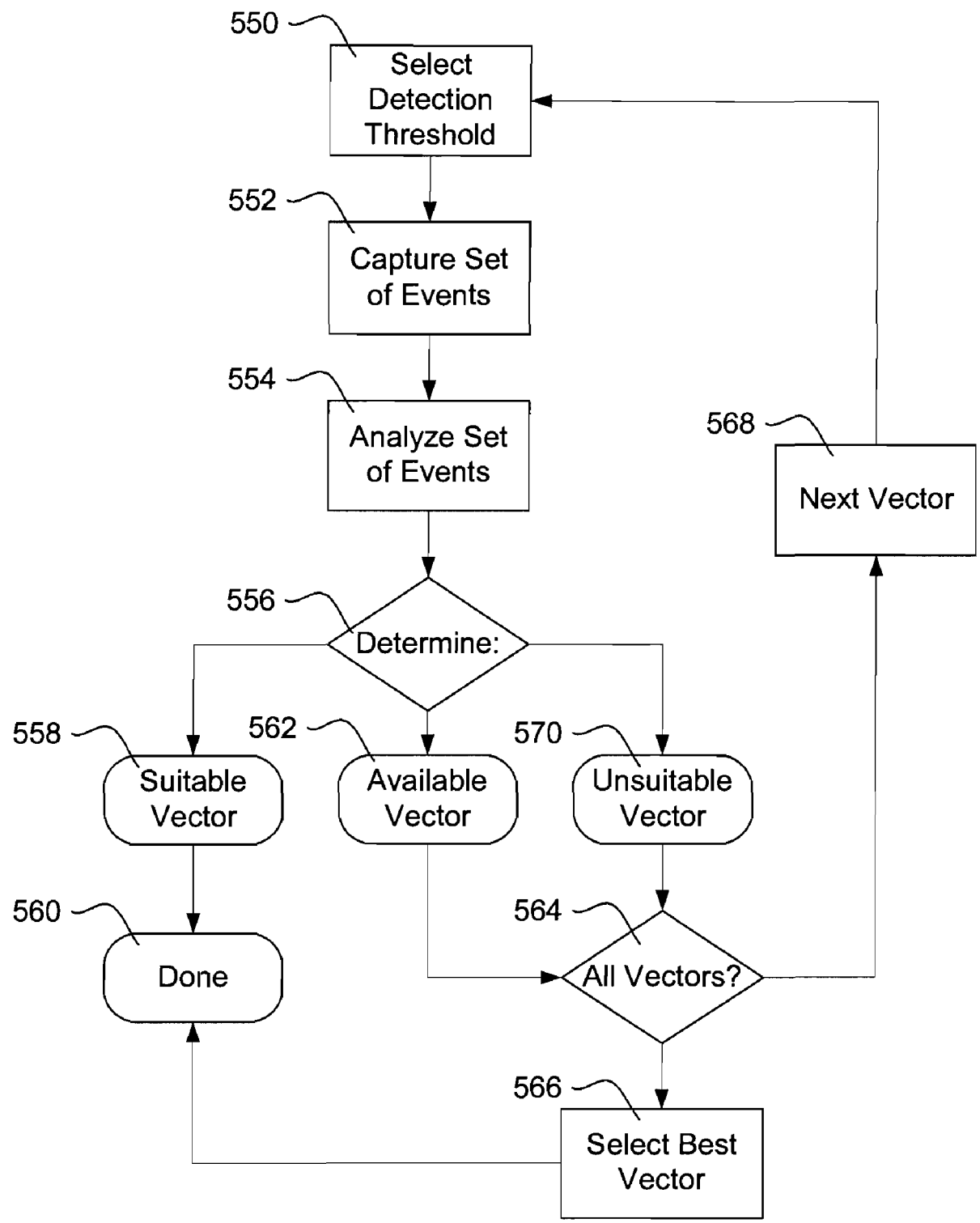
FIG. 13 is a block diagram for an illustrative embodiment.

FIG. 13 is a block diagram for an illustrative embodiment. Beginning at block 550, the method includes selecting a detection threshold. Next, a set of events is captured, as indicated at 552, using the detection threshold to define cardiac events sensed along a selected sensing vector. The set of events is analyzed as shown at 554. The analysis at 554 results in a determination at 556. The sensing vector used to capture the set of events at 552 is determined at step 556 to be one of a suitable vector, an available vector, or an unsuitable vector, as shown at 558, 562, and 570, respectively.

If the sensing vector is determined to be a suitable vector as shown at 558, then the sensing vector has been found to have met selected parameters for finding a suitable cardiac sensing vector. A vector meeting the selected parameters is, in the illustrative method, assumed to be likely sufficient to provide accurate cardiac monitoring. In the illustrative method, further consideration of additional sensing vectors is considered unnecessary. Therefore, as indicated at 560, the method ends without further analysis of additional sensing vectors. The suitable vector is then used for cardiac event detection and analysis.

If, instead, the sensing vector is determined to be an available vector, as shown at 562, then the vector under consideration is considered a candidate for data capture, but does not meet the parameters to render further consideration of additional sensing vectors unnecessary. Also, an available vector may be a sensing vector that indicates ambiguity in its analysis. The method then continues at 564, and determines whether all available sensing vectors have been analyzed. If so, the method continues to step 566, where the best vector is selected. Step 566 may include sub-methods to resolve ambiguities, if present, in the available vector(s). The method then ends at 560.

If not all sensing vectors have been considered when at step 564, the method continues by considering a different sensing vector, as indicated at 568. The method then returns to step 550 where a new detection threshold is selected for the "next" sensing vector.

Figure 14:
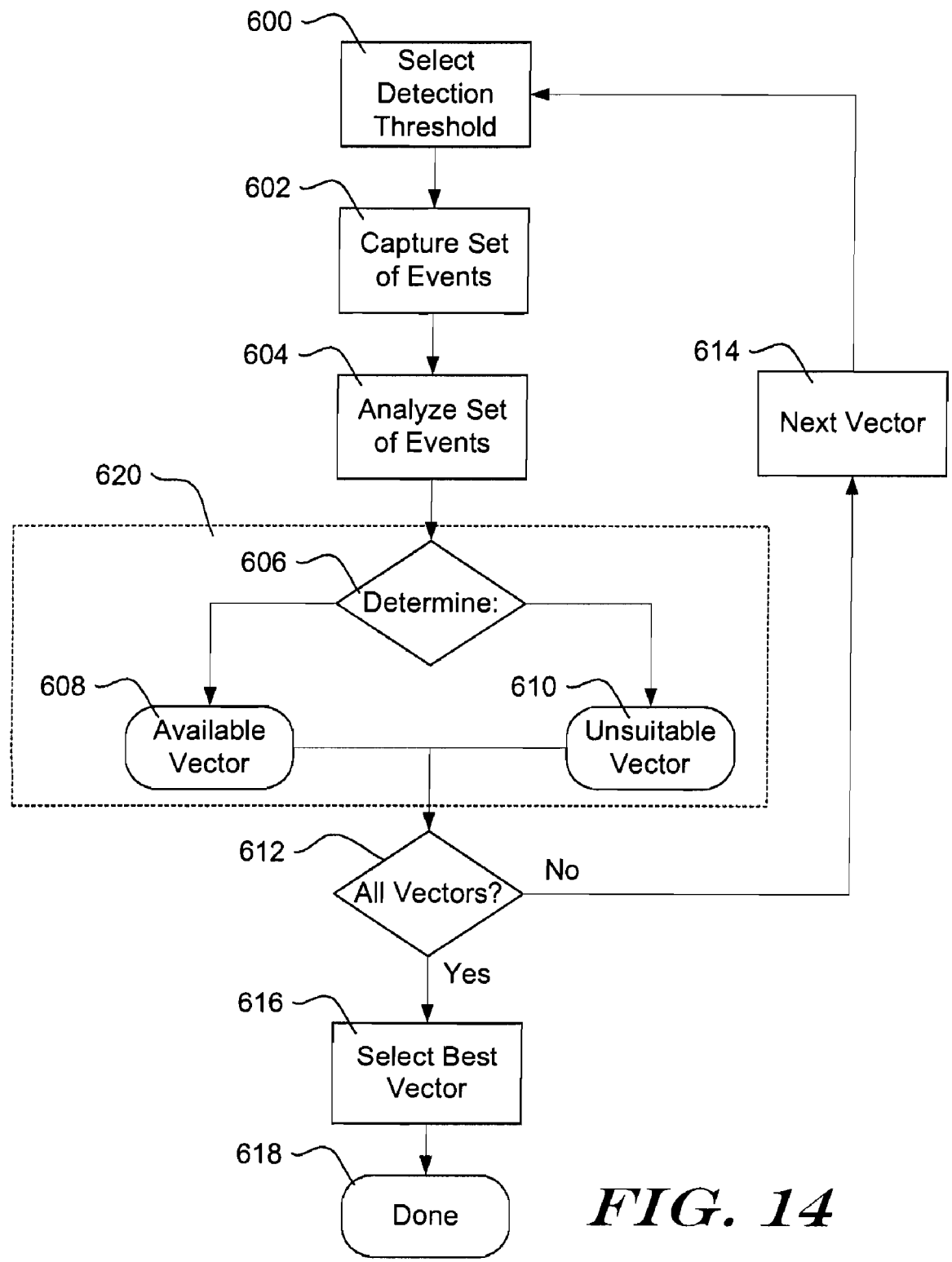
FIG. 14 is a block diagram for another illustrative embodiment.

FIG. 14 is a block diagram for another illustrative embodiment. In the illustrative method of FIG. 14, early exit conditions are not used to terminate vectoring analysis prior to analysis of each of the available vectors. It should be noted, however, that a determination may still be made as to which of the polarities of each vector will be analyzed, for example, by determining which polarity results in the greatest positive excursion from a baseline. In some systems, a rectified signal is used in analysis, such that the incoming polarity is not particularly important.

In the illustrative embodiment of FIG. 14, the method begins at step 600 where, as before, a detection threshold is identified. An adaptive or constant threshold may be selected, as desired. Next, a set of events is captured, as shown at 602. The set of events may be analyzed immediately, as shown at 604, or analysis can wait until all data capture for each vector or position is complete. An optional box is shown at 620, and includes the steps of determining the characteristics of each vector, as indicated at 606. In the illustrative embodiment, vectors are characterized as "available vectors," as shown at 608, or "unsuitable vectors" as shown at 610. The determination at 606 may be performed, for example, by comparing the SNR and/or peak amplitude of captured detections to one or more thresholds. Unsuitable vectors may be marked as such, and further/later analysis (for example, calculation of a SCORE) may be omitted for such vectors. The block at 620 is optional, and may be omitted in some embodiments.

Next, it is determined whether the capture step 602 has been performed for all available vectors, as indicated at 612. If not, the method returns to step 600, as indicated at 614. If all vectors have been considered at step 612, the method continues to step 616 where a best vector is selected, and the method ends, as indicated at 618.

The step of selecting a "best" vector may take several forms. In one illustrative embodiment, each vector is considered, for example, using a SCORE, and a highest "scoring" vector is selected. In embodiments where vectors may be marked as "available vectors" or "unsuitable vectors," only those vectors that are "available vectors" may be considered in selecting a "best" vector. Alternatively, individual vectors may be considered one at a time and compared to thresholds for each individual vector. This may allow preferential selection of a vector, even without the use of an early exit condition. If no threshold is exceeded, the highest scoring vector may be selected. In yet another embodiment, different vectors may undergo different scoring methods, either to preferentially identify a selected vector or to provide analysis that is particularly suited to individual vectors. For example, in a transvenous system, a first vector using the canister electrode and an intracardiac electrode may be considered more likely subject to noise than a second vector using two intracardiac electrodes. Calculation of a SCORE may take this into account by calculating the SCORE for the first vector differently than for the second vector.

For each of the above embodiments, certain additional steps may be undertaken to inform the operator (such as a physician performing an implant procedure or providing a patient check-up) about vector selection. For example, the selected vector may be characterized on the basis of its SCORE as "Good" or "Poor," for example. If the selected vector is "Good," then the system may, via an associated programmer, optionally provide an indication of such to the operator. Alternatively, no indication may be given, as no action is needed from the operator and the patient is apparently well suited to the device. If the selected vector is "Poor," and has a relatively low SCORE, the operator may be informed via the programmer. This allows the operator to determine, for example, if the patient is a very high risk subject, that the device should be explanted and a different treatment mode or device relied upon. The operator may also be prompted to perform an induction test (where fibrillation is induced in the patient) under controlled clinical conditions to determine whether the device can accurately detect the arrhythmia, even with the Poor sensing vector, and subsequently stimulate the patient out of the arrhythmia. The operator may also be able to determine if there is a cause for the Poor score, for example, incorrect placement of one or more electrodes or faulty operation of the device or a lead. The annunciation of sensing vector qualities is therefore another optional part of some illustrative methods, or may be a feature of some illustrative devices and/or systems.

The present invention includes certain embodiments in which the above methods may be performed by the implantable device in response to detected conditions, a request from an associated programmer, at intervals, or for other suitable reasons. Detected conditions prompting performance of vector analysis may include the occurrence of repeated difficulty with sensing, for example, the identification of an inordinate amount of double detections or a failure to consistently detect events. Another detected condition may be a rise in SNR or a drop in detected amplitude either below a predetermined level or to a level that creates sensing difficulties (for example, the range of 1.7 millivolts to 2.0 millivolts in a tiered sensor having 2.0 millivolt and 4.0 millivolt selectable dynamic sensing ranges).

These methods may be performed by an implantable cardiac stimulus device having a housing containing operational circuitry, or multiple housings tethered together containing operational circuitry distributed among the housings. The operational circuitry may be adapted to perform various of the above steps and methods using either or both of the analog and/or digital domain using appropriate components, devices, and connections, including but not limited to a microcontroller and associated memory.

In an illustrative embodiment in which one or more of the above methods are performed by an implantable medical device system, if it is determined that user input is needed to determine whether an identified largest possible score (LPS) corresponds to a score or a possible score, the method may include further steps. In particular, after the LPS is identified, it may be determined whether a programmer is currently in communication with the implantable medical device system. If so, then telemetry circuitry/devices are used to contact the programmer to request the user input. Otherwise, the implantable medical device system sets aside the LPS for later verification once a programmer is available for communication allowing the user input. If more than one LPS is larger than the largest available Score, information indicating the successive next LPS (or several LPS's) may be stored until communication with a programmer is available.

Further, the present invention includes embodiments in which at least certain steps of the above methods may be performed by a programmer adapted for use with an implantable medical device, the programmer being adapted to communicate (for such embodiments, communication is preferably but not necessarily wireless) with an implantable medical device. The programmer may comprise various appropriate components and circuitry for performing method steps. The programmer may direct operation of the implantable medical device to perform the method(s), or the programmer may use the implantable medical device to capture data from the patient and transfer the captured data to the programmer itself. In some embodiments, certain method steps (event detection, for example) may be performed by the implantable medical device while other steps (detected event analysis, for example) may be performed by the associated programmer.

The present invention also includes embodiments in which machine readable media encodes an instruction set or sets for performing the above methods using operational circuitry of an implantable medical device or, in some embodiments, using circuitry in a programmer for use in association with an implantable medical device.

Devices, including implantable medical devices and programmers, that are adapted to perform one or more steps of the above methods, as well as systems comprising implantable medical devices and programmers that are adapted as systems to perform any of these methods and/or steps, are also included in illustrative embodiments.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of selecting a default sensing vector for use with an implantable cardiac stimulus device system, the system comprising: an implantable medical device adapted to define a plurality of sensing vectors between electrodes implanted in a patient, and a programmer adapted for communication with the implantable medical device, the method comprising:

the implantable medical device capturing cardiac signal data using at least one of the plurality of sensing vectors;

(x) analyzing data related to the captured cardiac signal data to establish a set of detections separated by intervals, the set of detections including a first detection in time and a series of detections occurring after the first detection;

(y) analyzing the set of detections by identifying the first detection in time as a QRS peak and, for the remaining detections performing the following until a predetermined number of QRS peaks are identified:

comparing an interval from a preceding detection to a threshold and, if the threshold is exceeded, identifying a detection as a QRS peak; if not, comparing the interval from the preceding detection to a prior interval and (i) if the interval and the prior interval are similar within a boundary condition, advancing to amplitude analysis; if the prior interval is shorter outside the boundary condition, identifying a detection as a QRS peak; or, if the prior interval is longer outside the boundary condition, identifying a detection as a Noise Peak; and if consecutive detections are identified as QRS peaks, identifying a Noise peak therebetween;

if the step of comparing the intervals leads to amplitude analysis, performing the amplitude analysis by comparing the amplitudes of two detections to one another and binning the latter detection of the two detections according to whether it is approximately equal to, within predetermined bounds, larger than, or smaller than the earlier detection of the two detections; and if all of the detections have been analyzed in the comparing the interval step and less than a predetermined number of QRS peaks have been identified, determining whether a threshold number of detections are in the approximately equal to bin and, if so, declaring a bad vector;

otherwise, further parsing the detections by amplitude into QRS peaks and noise peaks and calculating a vector score using each of the average amplitudes of identified QRS peaks and Noise peaks in a polynomial formula;

(z) if a score is generated in step (y), comparing the score to a threshold and,
  (i) if the threshold is at least met, determining that an identified sensing vector is suitable for cardiac event detection; or
  (ii) if the threshold is not met, or if a bad vector is declared, determining that one or more other sensing vectors is to be analyzed.

2. The method of claim 1, wherein, if it is determined that one or more other sensing vectors is to be analyzed, the method further comprises:
  the implantable medical system capturing additional cardiac signal data using one or more other sensing vectors; and
  repeating steps (x), (y) and (z).

3. The method of claim 2, wherein if, after repeating steps (x), (y) and (z) for a number of vectors, no threshold is met by a score, the method further comprises:
  (a) if at least one score is generated, identifying a vector for which a highest score is generated as the best available sensing vector; or
  (b) if no scores are generated, requesting operator input to complete a sensing vector selection process.

4. The method of claim 3, wherein steps (x), (y), (z) and (a) are performed by the implantable medical device, and step (b) is performed using the programmer.

5. The method of claim 3, wherein steps (x), (y), (z), (a) and (b) are performed by the programmer.

6. The method of claim 1, wherein:
  the polynomial formula, includes at least first and second peaks with a valley therebetween, the valley corresponding to a limit of a signal input dynamic range of an ECG amplifier of the implantable medical device.

7. The method of claim 1, wherein the polynomial formula is a sixth order non-continuous polynomial.

8. An implantable medical device comprising a canister housing operational circuitry and at least first, second, and third electrodes useable by the operational circuitry for sensing cardiac activity when implanted in a patient, the operational circuitry being configured to perform cardiac signal analysis by the use of a selected sensing vector, wherein the operational circuitry is further configured to select a sensing vector from among at least first, second and third sensing vectors defined by the first, second and third electrodes by a vector selection method comprising:
  capturing cardiac signal data using at least one of the sensing vectors;
  (x) analyzing data related to the captured cardiac signal data to establish a set of detections separated by intervals, the set of detections including a first detection in time and a number of detections occurring after the first detection;
  (y) analyzing the set of detections by identifying the first detection in time as a QRS peak and, for the remaining detections performing the following until a predetermined number of QRS peaks are identified:
    comparing an interval from a preceding detection to a threshold and, if the threshold is exceeded, identifying a detection as a QRS peak; if not,
    comparing the interval from the preceding detection to a prior interval and if the interval and the prior interval are similar within a boundary condition, advancing to amplitude analysis; if the prior interval is shorter outside the boundary condition, identifying a detection as a QRS peak; or, if the prior interval is longer outside the boundary condition, identifying a detection as a Noise Peak; and
    if consecutive detections are identified as QRS peaks, identifying a Noise peak therebetween;
    if comparing the intervals leads to amplitude analysis, performing the amplitude analysis by comparing the amplitudes of two detections to one another and binning the latter detection of the two detections according to whether it is approximately equal to, within predetermined bounds, larger than, or smaller than the earlier detection of the two detections; and
    if all of the detections have been analyzed in the comparing the interval step and less than a predetermined number of QRS peaks have been identified, determining whether a threshold number of detections are in the approximately equal to bin and, if so, declaring a bad vector;
    otherwise further parsing the detections by amplitude into QRS peaks and Noise peaks and calculating a vector score using each of the average amplitudes of identified QRS peaks and Noise peaks in a polynomial formula;
  (z) if a score is generated in step (y), comparing the score to a threshold and,
    (i) if the threshold is at least met, determining that an identified sensing vector is suitable for cardiac event detection; or
    (ii) if the threshold is not met, or if a bad vector is declared, determining that one or more other sensing vectors is to be analyzed.

9. The device of claim 8, wherein the operational circuitry is further configured such that, if it is determined that one or more other sensing vectors is to be analyzed, the vector selection method further comprises:
  capturing additional cardiac signal data using one or more other sensing vectors; and
  repeating steps (x), (y) and (z).

10. The device of claim 9, wherein the operational circuitry is further configured such that, if, after repeating steps (x), (y) and (z) for a number of vectors, no threshold is met by a score, the vector selection method further comprises:
  (a) if at least one score is generated, identifying a vector for which a highest score is generated as the best available sensing vector; or
  (b) if no scores are generated, requesting operator input to complete a sensing vector selection process.

11. The device of claim 8, further comprising telemetry circuitry configured for communication with a programmer, wherein the operational circuitry is configured to perform the vector selection method in response to prompting by the programmer.

12. The device of claim 8, wherein the operational circuitry is configured to perform the vector selection method periodically.

13. The device of claim 8, wherein the operational circuitry is configured to perform the vector selection method occasionally if occasions of sensing error or cardiac event detection error occur.

14. The device of claim 8, wherein the operational circuitry is further configured such that:
  the polynomial formula includes first and second polynomials and includes at least first and second peaks with a valley therebetween, the valley corresponding to a limit of a signal input dynamic range of an ECG amplifier making up part of the operational circuitry.

15. The device of claim 8, wherein the operational circuitry is further configured such that the polynomial formula includes a sixth order non-continuous polynomial making use of an average Signal Amplitude for the series of detections.

16. A system for implantable cardiac monitoring and stimulus comprising:
- an implantable medical device including a canister housing operational circuitry, the operational circuitry including telemetry circuitry, the device further comprising at least first, second and third electrodes usable as sensing electrodes by the operational circuitry; and
- a programmer configured to communicate with the telemetry circuitry of the implantable medical device;
- wherein the system is configured to perform a vector selection method for selecting from among a plurality of sensing vectors defined between the first, second and third electrodes, the vector selection method comprising:
- capturing cardiac signal data using at least one of the sensing vectors;
- (x) analyzing data related to the captured cardiac signal data to establish a set of detections separated by intervals, the set of detections including a first detection in time and a number of detections occurring after the first detection;
- (y) analyzing the set of detections by identifying the first detection in time as a QRS peak and, for the remaining detections performing the following until a predetermined number of QRS peaks are identified:
  - comparing an interval from a preceding detection to a threshold and, if the threshold is exceeded, identifying a detection as a QRS peak; if not,
  - comparing the interval from the preceding detection to a prior interval and if the interval and the prior interval are similar within a boundary condition, advancing to amplitude analysis; if the prior interval is shorter outside the boundary condition, identifying a detection as a QRS peak; or, if the prior interval is longer outside the boundary condition, identifying a detection as a Noise Peak; and
  - if consecutive detections are identified as QRS peaks, identifying a Noise peak therebetween;
  - if comparing the intervals leads to amplitude analysis, performing the amplitude analysis by comparing the amplitudes of two detections to one another and binning the latter detection of the two detections according to whether it is approximately equal to, within predetermined bounds, larger than, or smaller than the earlier detection of the two detections; and
  - if all of the detections have been analyzed in the comparing the interval step and less than a predetermined number of QRS peaks have been identified, determining whether a threshold number of detections are in the approximately equal to bin and, if so, declaring a bad vector;
  - otherwise further parsing the detections by amplitude into QRS Peaks and Noise peaks to calculate a vector score using each of the average amplitudes of identified QRS peaks and Noise peaks in a polynomial formula;
- (z) if a score is generated in step (y), comparing the score to a threshold and,
  - (i) if the threshold is at least met, determining that an identified sensing vector is suitable for cardiac event detection; or
  - (ii) if the threshold is not met, or if a bad vector is declared, determining that one or more other sensing vectors is to be analyzed.

17. The system of claim 16, wherein, if it is determined that one or more other sensing vectors is to be analyzed, the selection method further comprises:
- capturing additional cardiac signal data using one or more other sensing vectors; and
- repeating steps (x), (y) and (z).

18. The system of claim 17, wherein if, after repeating steps (x), (y) and (z) for a number of vectors, no threshold is met by a score, the selection method further comprises:
- (a) if at least one score is generated, identifying a vector for which a highest score is generated as the best available sensing vector; or
- (b) if no scores are generated, requesting operator input to complete a sensing vector selection process.

19. The system of claim 18, wherein steps (x), (y), (z) and (a) are performed by the implantable medical device, and step (b) is performed using the programmer.

20. The system of claim 18, wherein steps (x), (y), (z), (a) and (b) are performed by the programmer.

* * * * *